US009459194B2

(12) United States Patent
Benner et al.

(10) Patent No.: US 9,459,194 B2
(45) Date of Patent: Oct. 4, 2016

(54) APPARATUSES, PROCESSES, AND SYSTEMS FOR MEASURING PARTICLE SIZE DISTRIBUTION AND CONCENTRATION

(71) Applicant: CARDIO METRIX, Pleasanton, CA (US)

(72) Inventors: William Henry Benner, Danville, CA (US); Donald John Holve, Berkeley, CA (US)

( * ) Notice: Subject to any disclaimer, the term of this patent is extended or adjusted under 35 U.S.C. 154(b) by 419 days.

(21) Appl. No.: 14/147,482

(22) Filed: Jan. 3, 2014

(65) Prior Publication Data

US 2014/0260702 A1 Sep. 18, 2014

Related U.S. Application Data

(60) Provisional application No. 61/781,734, filed on Mar. 14, 2013.

(51) Int. Cl.
*G01N 15/10* (2006.01)
*G01N 15/02* (2006.01)
*G01N 15/00* (2006.01)
*G01N 1/22* (2006.01)

(52) U.S. Cl.
CPC ... *G01N 15/0266* (2013.01); *G01N 2001/2223* (2013.01); *G01N 2015/0046* (2013.01); *G01N 2015/0053* (2013.01)

(58) Field of Classification Search
None
See application file for complete search history.

(56) References Cited

U.S. PATENT DOCUMENTS 3,845,301 A 10/1974 Wernlund
4,777,363 A 10/1988 Eiceman
5,719,392 A 2/1998 Franzen
5,747,799 A 5/1998 Franzen
5,905,258 A 5/1999 Clemmer
5,936,242 A 8/1999 De La Mora
5,949,001 A 9/1999 Willeke
5,969,349 A 10/1999 Budovich
6,012,343 A 1/2000 Boulaud
6,051,832 A 4/2000 Bradshaw
6,229,143 B1 5/2001 Wernlund
6,230,572 B1 * 5/2001 Pui et al. .................. 73/863.21
6,263,744 B1 7/2001 Russell
6,323,482 B1 11/2001 Clemmer
6,389,912 B1 5/2002 Wood
6,408,704 B1 6/2002 Willeke
6,412,359 B1 7/2002 Zborowski
6,418,802 B1 7/2002 Wood
6,491,872 B1 12/2002 Wick
6,498,342 B1 12/2002 Clemmer
6,583,407 B1 6/2003 Fischer
6,586,732 B2 7/2003 Lee
6,593,567 B1 7/2003 Abdel-Rahman
6,601,464 B1 8/2003 Downing
6,748,815 B2 6/2004 Povey
(Continued)

*Primary Examiner* — Robert R Raevis
(74) *Attorney, Agent, or Firm* — Mardson Q. McQuay

(57) ABSTRACT

Apparatuses, methods, and systems are disclosed for analyzing particles from about 0.001 to about 1 μm in diameter by controlling a gaseous medium through which the particles travel so that properties of the particles, such as diameter, electrical mobility, and charge, are measured. One embodiment of the disclosed apparatuses includes a particle source generator, a nozzle, a chamber, an electronic gate, and a detector. Resolution of the measurements made by the disclosed apparatuses is improved by use of a mathematical deconvolution of a spread in arrival times generated by particles of different sizes and charge levels and non-ideal background flow velocity variations.

20 Claims, 21 Drawing Sheets

(56) References Cited

U.S. PATENT DOCUMENTS

| | | | | |
|---|---|---|---|---|
| 6,796,195 | B2 | 9/2004 | Povey | |
| 6,809,314 | B2 | 10/2004 | Yamada | |
| 6,829,955 | B1 | 12/2004 | Mahgerefteh | |
| 6,862,536 | B2 | 3/2005 | Rosin | |
| 6,919,367 | B2 | 7/2005 | Bacon | |
| 6,931,950 | B2 | 8/2005 | Malachowski | |
| 6,959,618 | B1 | 11/2005 | Larsen | |
| 7,066,037 | B2 | 6/2006 | Keskinen | |
| 7,140,266 | B2 | 11/2006 | Marjamaki | |
| 7,164,122 | B2 | 1/2007 | Fuhrer | |
| 7,213,475 | B2 | 5/2007 | Coghill | |
| 7,213,476 | B2 | 5/2007 | Cheng | |
| 7,244,931 | B2 | 7/2007 | Zimmermann | |
| 7,259,018 | B2 * | 8/2007 | Benner et al. | 436/71 |
| 7,268,347 | B1 | 9/2007 | Blanchard | |
| 7,298,127 | B2 | 11/2007 | Golder | |
| 7,713,744 | B2 * | 5/2010 | Benner et al. | 436/71 |
| 7,851,224 | B2 * | 12/2010 | Benner et al. | 436/71 |
| 2001/0032930 | A1 | 10/2001 | Gillig | |
| 2002/0011560 | A1 | 1/2002 | Sheehan | |

* cited by examiner

APPARATUSES, PROCESSES, AND SYSTEMS FOR MEASURING PARTICLE SIZE DISTRIBUTION AND CONCENTRATION

CROSS REFERENCE TO RELATED APPLICATIONS

This application claims priority to U.S. patent application of Ser. No. 61/781,734, filed on Mar. 14, 2013, entitled "Apparatuses, Processes, and Systems for Measuring Particle Size Distribution and Concentration," the contents of which are herein incorporated by reference in their entirety.

STATEMENT ABOUT FEDERALLY SPONSORED RESEARCH

At least part of the materials disclosed herein was made with Government support under Contract No. 1 R43 HL080933-01. As such, the Government may have certain rights therein as provided for by the terms of these contracts.

BACKGROUND

1. Technical Held

Embodiments of the subject matter disclosed herein relate generally to apparatuses, methods and systems and, more particularly, to devices, processes, mechanisms and techniques for measuring size distribution and/or concentration of particles.

2. Description of Related Art

The ability to measure and to quantify the type, behavior, and/or characteristics of particles (e.g., measurement of individual size and local number and/or mass concentrations) is of utmost importance in a large number of applications of interest, including, for example, medical diagnostics, food preparation, environmental sciences in general, and the control of industrial and vehicular emissions, to name just a few. More specifically, in the medical diagnostics area, for example, it is well established that a risk for a particular disease (e.g., Coronary Heart Disease, or CHD) can be reasonably assessed by measuring mobility spectra (i.e., the mass distribution as a function of particle size) of lipoprotein particles in the blood of a patient. There are also many other medical diagnostics that are based on the ability to measure protein sizes and concentrations, including the ability to identify a genetic disease based on the variation of size and concentration of hemoglobin. In addition, in the area of aerosol and nanotechnology sciences, as applied to environmental concerns, for example, there exist several requirements to measure the size and/or type of a particle that can be related to emissions controls, environmental measurements of how much soot or particulate matter a person may be exposed to in ambient airflows, how much dust may be exhausting into the atmosphere from industrial source emissions, or the quantification of size and concentration of particulate matter in the atmosphere and their effect on the earth's climate. The need to perform particle-related measurement is further evidenced by the large number, and ever more stringent, governmental regulations dealing with the subject.

A variety of measurement techniques have been used to determine the size of particles smaller than 1 μm in diameter. Optical particle detectors determine particle size from the amount of light scattered into a photodetector when a particle passes through a single laser beam. This method is limited to particles larger than about 0.05 μm in diameter. Aerodynamic particle-acceleration lens systems have been designed to accelerate particles according to their size—smaller particles attaining higher velocity than larger particles when a gas containing such particles is accelerated through a nozzle. When the accelerated particles are directed to pass through two precisely spaced laser beams, light scattered by the transiting particle produces two pulses on a photodetector, thus revealing the time it takes a particles to pass through the two laser beams, from which particle velocity can be deduced. This technique is also limited to particles larger than about 0.05 μm in diameter. Aerosol impactors can be used to deposit selected sizes of particles onto a collection surface or into a collection fluid. Chemical analysis and the weight of the collected particles can then be used to construct particle size distributions.

In applications involving macromolecules (e.g., DMA, RNA, and proteins, including their fragments as well as small particles less than 100 nm in diameter), several conventional sizing techniques and/or devices are known, namely, gel electrophoresis, Differential Mobility Analyzers (or DMA), drift tubes, and mass spectrometers, although the latter is used to determine the size of molecules, it actually provides only molecular mass.

Gel electrophoresis is used in clinical chemistry to separate proteins by charge and or size and in biochemistry and molecular biology to separate a mixed population of DNA and RNA fragments by length, to estimate the size of DNA and RNA fragments, or to separate proteins by charge. Nucleic acid molecules are separated by applying an electric field to move the negatively charged molecules through a gel matrix. Shorter molecules move faster and migrate farther than longer ones because shorter molecules migrate more easily through the pores of the gel. Gel electrophoresis can also be used for separation of nanoparticles. Those of ordinary skill will however recognize that gel electrophoresis is a technique that requires a substantial amount of time for completion of any given measurement. Additionally, the position of a band in a gel electrophoresis lane needs to be compared to size standards, typically molecules of known molecular weight, in order to estimate the molecular weight of the material in the band. The need to calibrate gel lanes adds to the effort involved and makes the method a relative measurement technique.

Differential electrical mobility analyzers may be used to determine the size distribution of particles smaller than a micrometer in diameter, in this method, a cloud of charged aerosol particles is drawn between two electrodes, such as the annular space between two concentric cylinders. Voltage applied to the cylinders deflects particles of a predictable size into a particle detector. By scanning the voltage applied to the cylinders, the size distribution of the particles is obtained. U.S. Pat. No. 6,230,572 (which is incorporated herein by reference in its entirety) discloses an example of such an apparatus.

It has been shown (see, for example, U.S. Pat. Nos. 7,259,018, 7,851,224, and 7,713,744, the entire contents of which are incorporated herein by reference) that electrical mobility spectra of lipoprotein particles isolated from human serum reveal simultaneously the size distributions of HDL, LDL, IDL and VLDL particles in a plasma sample, thus revealing a useful technique for assessing risk of CHD. The capability of mobility measurements to span the HDL and LDL lipoprotein size range in one spectrum may be one of the advantages of the use of mobility technology. Conventional gel electrophoresis systems require two different types of gels to reveal the size distributions of HDL particles separately (Agar gel) from LDL, IDL and VLDL particles (gradient density polyacrylamide gel). An example of a conventional measurement of the mobility spectra of lipoproteins obtained from five patients participating in a cholesterol study is illustrated in FIG. 1. The patients were selected on the basis of gel-derived lipoprotein patterns that characterized three of the patients at risk for CHD (type B pattern at high risk for CHD), two of the patients with lower risk for CHD (type A pattern at lower risk for CHD) and one patient having an intermediate risk. Ion mobility spectra provided data to predict the same level of risk for each patient. Mobility-derived lipoprotein profiles, such as these, are acquired substantially faster than those obtained by gel electrophoresis used to separate lipoprotein subclasses. However, those of ordinary skill in the art will appreciate that conventional DMA technology faces several challenges, including limited resolution to resolve profiles of lipoprotein particles that confer diagnostic value when measured using other techniques, such as gradient gel electrophoresis, and high capital and operating costs.

Another conventional device used to make measurements of ions is a drift tube. FIG. 2 illustrates a conventional cylindrical drift tube 10. In operation, voltage is applied to each of the ring-shaped electrodes 12 in such a way that the resulting electrical field inside the drift tube is constant along the longitudinal axis of the tube. An ion gate 14 is placed at the entrance to the drift tube and provides a way to introduce a pulse of ions 15 from an ion source 18 into the electric field generated inside the drift tube. In the example illustrated in FIG. 2, the ion population is bimodal, i.e., it comprises a group of heavy ions 20 and another of light ions (22). An ion detector 18 is located at the opposite end of the drift tube and responds to ions when they strike the detector, in the exemplary illustration of FIG. 2, the detector is a flat metal plate to which a current amplifier is connected and when a pulse of charged particles hits the detector, a momentary rise in detector current is observed, as illustrated in the Time-of-Flight (or TOF) spectrum 24 inserted in FIG. 2 for the bimodal ion group considered for this example, ion drift tubes are commonly purged with a flow of gas to minimize the influence of solvent vapor on drift time. Ion velocities resulting from the electrical field inside the drift tube are substantially higher than gas velocities in the purge gas and, as a consequence, gas velocity has little influence on ion trajectories and does not significantly impact ion arrival time distributions. However, the performance of conventional drift tubes for particles having drift velocities close to the velocity of the purge gas is substantially degraded, as understood by those of ordinary skill in the applicable arts.

Therefore, based at least on the above-noted challenges with conventional devices to measure the concentration and size of particles, it would be advantageous to have improved devices to accomplish the summarized tasks, among others, with increased measurement accuracy (particularly in embodiments operating on first principles without the need for calibration), lower cost of manufacturing and operation, reduction on the time required for measurements, and minimization or elimination of the effect of purge gas velocity on the velocity of the particles being measured, while, in some embodiments of the subject matter disclosed herein, increasing the resolution of such measurements by mathematically deconvolving from the measurements the effect of a spread in arrival times due to diffusion and non-ideal background flow velocity variations.

SUMMARY

One or more of the above-summarized needs or others known in the art are addressed by apparatuses, methods, and processes to measure average size and concentration of particles as disclosed herein. These apparatuses include a body defining a flow chamber, an exhaust port disposed on the distal end portion of the body; a particle detector disposed inside of the chamber; a focusing electrode disposed inside of the chamber; an electronic gate disposed downstream of the focusing electrode, the focusing electrode and the electronic gate further dividing the chamber into a jet relaxation region a drift region; a plurality of electrodes disposed on the body in the drift region downstream of the electronic gate; and a timing device configured to measure a time taken by the charged particles to travel from the electronic gate to the detector, wherein a measurement of the size and concentration of the charged particles is based on an output signal from the detector and the time measured by the timing device.

The subject matter disclosed herein also includes methods and processes to measure size and concentration of particles. These methods and processes include generating charged particles with a particle source; introducing these particles into a flow chamber of a drift tube; reducing the velocity of the charged particles while the particles are maintained substantially along a centerline of the chamber; controlling the flow of the particles with an electronic gate; controlling the drift velocity of the particles allowed to pass through the electronic gate; measuring the time taken by the charged particles to travel from the exit of the electronic gate to a particle detector disposed at an end portion of the flow chamber; and measuring a current generated by the charged particles impacting the particle detector, wherein a measurement of size and concentration of the charged particles is based on the current generated by the charged particles and the time taken the charged particles to travel from the electronic gate to the detector.

BRIEF DESCRIPTION OF THE DRAWINGS

The accompanying drawings (not drawn to scale), which are incorporated in and constitute a part of the specification, illustrate one or more embodiments and, together with the description, explain these embodiments. In the drawings.

DETAILED DESCRIPTION

Figure 1:
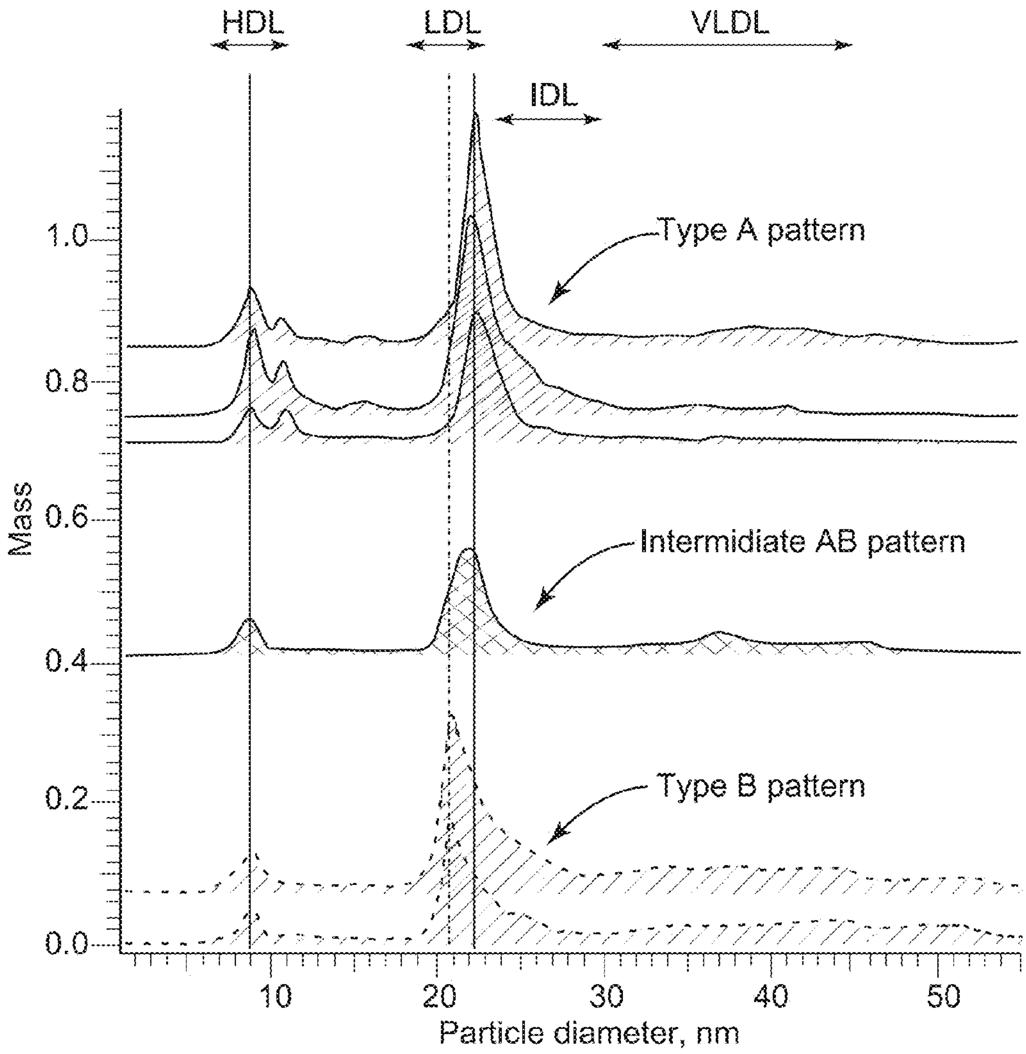
FIG. 1 illustrates the results of a conventional measurement of the mobility spectra of lipoproteins obtained from five patients participating in a cholesterol study.
Figure 2:
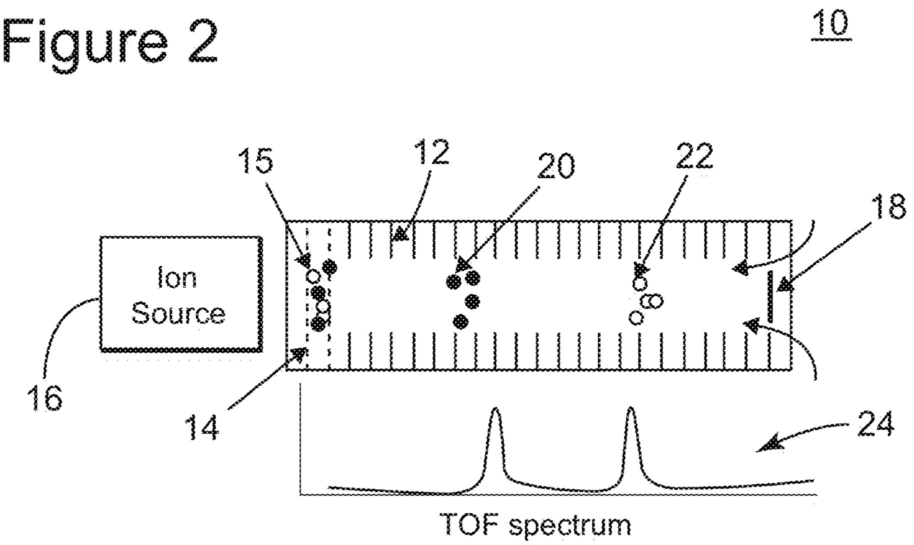
FIG. 2 illustrates a simplified diagram of a conventional ion drift tube.

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to the terminology and structure of apparatuses, systems, or methods for measuring size and concentration of charged particles. However, the embodiments to be discussed next are not limited to these sets, but may be applied to other apparatuses, systems, or methods, including, but not limited to, the measurement of aerosol particle diameter, the measurement of the size distribution of clouds of aerosol particles, the determination of the concentration of particles suspended in a gas, the determination of size and concentration of particles in a liquid by transferring them out of the liquid and into a gas and then analyzing them, and the determination of additional properties of the particles by first separating particles according to their size before they are presented to ancillary analytical methods, such as mass spectrometry, laser induced fluorescence spectrometry and light scatter. In other embodiments the subject matter disclosed extends ion mobility spectrometry and ion drift tubes to the analysis of particles, which cannot be accomplished with current ion mobility spectrometers or ion drift tubes.

As used herein throughout, the term “particle” includes all forms of minute quantities of materials smaller than one micrometer in diameter and suspended in a gas or liquid. The materials may include pure substances, such as any molecule or clusters of identical molecules characterized with a molecular weight. The materials may also include mixtures of materials, such as lipoprotein particles, soot particles, paint droplets, or smoke particles. The term charged-particle refers to any minute form of material that carries an electric charge such as a lipoprotein particle with excess positive or negative charges. Examples of particles include, but are not limited to, particles isolated from a human or an animal serum, particles released from a combustion process, smoke particles, dust particles, nanoparticles, assemblies of molecules, clusters of protein and/or lipid molecules, atmospheric aerosols, nanolipid particles, nanolipid disks, and dumps of such particles. Particles also include charged ions having a molecular weight less than $3\times10^{11}$ Daltons, equivalent to a 1 micrometer diameter particle.

Reference throughout the specification to “one embodiment” or “an embodiment” means that a particular feature, structure, or characteristic described in connection with an embodiment is included in at least one embodiment of the subject matter disclosed. Thus, the appearance of the phrases “in one embodiment” or “in an embodiment” in various places throughout the specification is not necessarily referring to the same embodiment. Further, the particular features, structures, or characteristics may be combined in any suitable manner in one or more embodiments.

Figure 3:
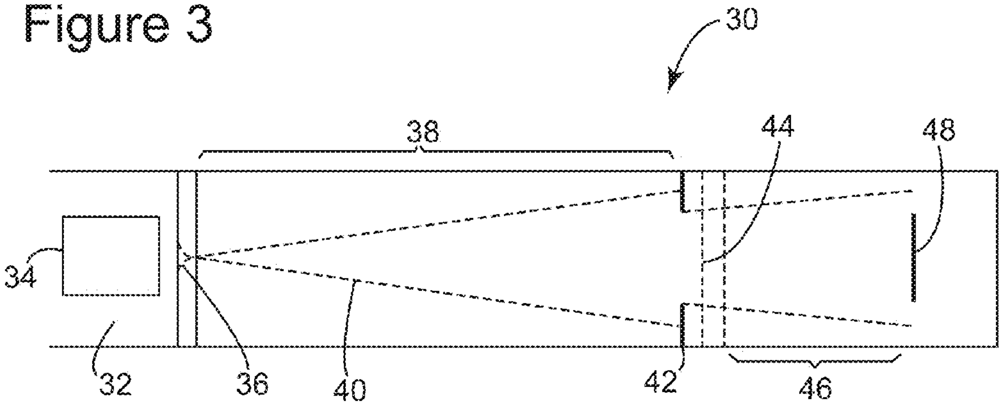
FIG. 3 illustrates a drift tube according to one exemplary embodiment of the subject matter disclosed.

An exemplary embodiment of a drift tube 30 according to the subject matter disclosed is illustrated in FIG. 3. As shown, a charged particle generator 34 (as, for example, an electrospray source, a nebulizer, a flame, a grinding wheel, a combustion engine, or a gas-phase chemical reactor) disposed in a region of atmospheric pressure 32 generates particles that are introduced through a nozzle 36 in the form of a particle-laden jet 40 at high velocities into the body of the drift tube 30, this body defining a chamber in which the charged particles flow. As illustrated, in the first portion of the chamber, a jet relaxation region 38 is formed which is configured to reduce the velocity of the particles while maintaining them along the centerline of region 38. In some embodiments the nozzle 38 is adjustable with respect to nozzle diameter and position within the jet relaxation region 38 so as to allow better control of the gas velocity in the drift tube 30. As the particle-laden jet 40 flows into the jet relaxation region 38, in view of the large injection velocity through the nozzle 38, the particles remain near the centerline and produce a final flow field in the drift region 46 that is at low pressure and nearly uniform with respect to the radial velocity profile, in this manner, the jet relaxation region 38 helps to establish conditions that introduce particles into the drift region 46 of the flow chamber and eliminate and/or substantially reduce the influence of gas velocity on the dynamic behavior of the particles to be measured. Conditions of low gas velocity and pressure are desirable so that gas velocity is substantially lower (i.e., having velocities less than 90% of the slowest particles) than the drift velocities of the particles, thus minimizing the influence of the background gas on particle motion.

After the jet relaxation region 38, the particles flow through a focusing electrode 42 configured to minimize and/or eliminate the tendency of the jet flow to cause the particles to diverge from the centerline of the drift region 48 of the tube 30, thereby guiding more particles onto a target area, as further explained below, for the purpose of improving detection efficiency. Although the embodiment illustrated in FIG. 3 includes only one focusing electrode, it should be understood that the scope of the subject matter disclosed herein includes embodiments that use a multiplicity of focusing electrodes. After the focusing electrode 42 the particles then pass through an electronic gate 44 configured to stop the flow of particles until sufficient particles accumulate in that position before they are allowed to move forward in the drift region 46. As explained further below, the scope of the subject matter disclosed includes several embodiments of the electronic gate 44, including those having a bi-functional operation. Once the particles pass the electronic gate 44, an electric field generated by electrodes (not shown in FIG. 3) configured to control the velocity of the particles in the drift region 48 of the drift tube 30 causes the particles to drift towards a defector 48 faster than the background gas. The detector 48 is configured to measure the rate for the particles to travel from the electronic gate 44 to the detector 48. Measurement of this rate along with knowledge of the distance between the electronic gate 44 and the detector 48, gas pressure, and gas velocity produces the desired signals that can be converted into the size and concentration of the particles being measured, as it will be further explained below, in addition, as it will be further discussed below, in some embodiments, numerical prediction of particle velocity using computational fluid dynamics and the measured time it takes the particles to flow from the electronic gate 44 to the detector 48 can be used to correct the effect of background gas velocity on the measurements of particle electrical mobility by use of an advantageous deconvolution technique.

By substantially reducing the pressure from the atmospheric pressure region 32 to the jet relaxation region 38, the challenge of measuring particles having low drift velocities (for example, particles in the lipoprotein size range) is eliminated and/or substantially ameliorated because aerodynamic drag is reduced, thus allowing particles to travel faster for a given electric field strength than the background gas velocity, it is known that drift velocity scales inversely with pressure, and to a first approximation, gas flow velocity in the drift region also scales inversely with pressure. One of the advantageous aspects of operation at reduced pressure is that the jet relaxation region 38 provides a method of transition and transport of charged particles into a uniform low velocity gas, along with acceptable drift times for the particles (for example, drift times on the order of 400 ms in some embodiments). Embodiments similar to the one illustrated in FIG. 3 are thus capable of transporting a gas at atmospheric pressure, along with charged and uncharged particles entrained in the gas, through an orifice and into a drift tube maintained at reduced pressure.

In one embodiment, an electrospray source is used for generating charged particles suspended in a gas. Particles flow through the nozzle 36 (which, in one embodiment, comprises a small orifice having a diameter in the range of about 10 to about 1000 microns or preferably from about 200 to about 600 microns) at sonic velocity, where the downstream pressure in the jet relaxation region 38 is any value less than 0.5 bar so as to assure choked flow conditions at the nozzle 36, i.e., the gas jet and particles have sonic velocities at the point of minimum area of the nozzle 36. Downstream of the nozzle 36, the particle-laden jet 40 expands, with axial velocities decreasing to values of about 1 m/s within a short distance (e.g., less than 20 cm axial distance), which is approximately the location of the focusing electrode 42 illustrated in FIG. 3. Those of ordinary skill in the art will understand that these figures are exemplary only and should not be considered as limiting the subject matter disclosed in any way.

Placement of the electrodes for the electronic gate 44 (or gate electrodes) downstream of the focusing electrode 42 in a region where the axial jet velocity is relaxed to lower values, as explained, allows the charged particles flowing near the centerline of the particle-laden jet 40 to be stopped by the voltage applied to the electronic gate 44. In some embodiments, the electronic gate 44 is held at this voltage for a period of time ranging from about 0.01 to about 10 seconds, so that the flow of charged particles can be collected at this gate position, increasing the ultimate signal levels of charged particles arriving at the detector 48, following their release from the region near the electronic gate 44.

Those of ordinary skill in the applicable arts will appreciate that, during the time particles are accumulated in the electronic gate 44, particle diffusion will tend to disperse the charged particles radially, although the focusing electrode 42 around the region where the electronic gate 44 is located will help to confine incoming charged particles around the centerline of the jet. After sufficient charged particles have been collected, the voltage of the gate electrode 44 and the focusing electrode 42 is raised above the voltage needed to stop charged particles to initiate the drift of all particles towards the detector 48. By proper choice of the various physical characteristic of the drift tube 30 (such as overall length and diameter), all particles in the range from about 5 to about 50 nm will have drift velocities greater than or equal to the background gas flow velocity, for example, about 30 cm/s, and travel nearly straight towards the detector Those of ordinary skill in the applicable arts will also appreciate, after consideration of the subject matter disclosed herein, that the use of a nozzle and the subsequent jet expansion into an area of low pressure provides several benefits as compared to conventional designs. First, the particle laden jet transitions to the low pressure drift tube environment and the gas-particle interactions confine the particles near to the tube centerline, allowing for the particles to drift in a near-uniform electric field in the central core of the drift tube 30. Secondly, the expanding jet provides a way to reduce gas velocity, so that the gas velocity is small compared to the ultimate particle drift velocity in the drift region of the instrument. Thirdly, the diameter of the orifice may be chosen (e.g., values in a range from about 10 to about 1000 microns, or, preferably, from a range from about 200 to about 600 microns) to achieve sufficient flow of charged particles to give adequate signal at the current sensing detector 48, yet not too large a flow that increases the background gas flow velocity in the drift region 46. Indeed the final diameter of the drift tube (e.g., a value around 7 cm for some embodiments) may be selected so as to maintain a low background flow velocity). Fourthly, the exit pressure of the drift tube may be defined by a vacuum pump, which can readily achieve pressures below 0.01 atm in some embodiments, giving higher drift velocities and thus shorter analysis times. Vacuum pump operating pressures in the range from about 0.1 to about 0.01 atm may be used in some applications. Fifthly, the overall length of the instrument (jet relaxation region 38 plus the drift region 46) may be chosen to be about 35 cm and the flow tube diameter to be about 7 cm, thus resulting in transition of particles across the jet relaxation region in about 25 ms, while drift times may range in some embodiments from about 5 ms for 5 nm singly-charged particles to about 200 ms for 50 nm singly-charged particles at an operating pressure of about 0.03 bar, a drift tube length of about 9 cm, and an electric field of about 1 kV/cm.

Figure 4:
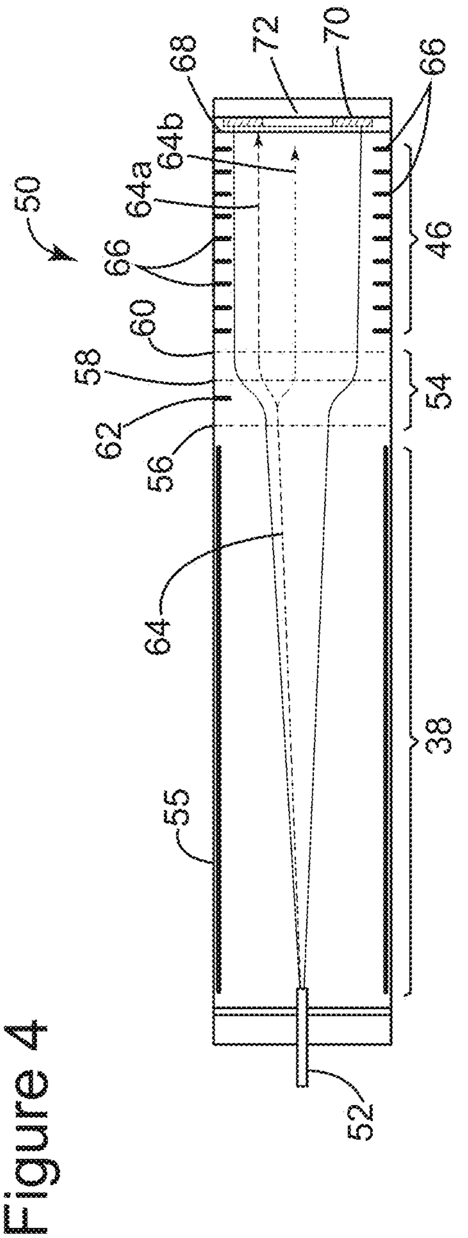
FIG. 4 illustrates another drift tube according to another exemplary embodiment of the subject matter disclosed.

FIG. 4 illustrates a drift tube 50 according to another exemplary embodiment of the subject matter disclosed. As shown, an inlet tube 52 is used to introduce charged particles from a particle generator (not shown), such as an electrospray source, into a jet relaxation region 38 around which a tubular electrode 55 is disposed so as to prevent charged particles that are too small from flowing into the drift tube 50 and affecting the final measurements. In this embodiment, the inlet tube 52 is disposed with a nozzle for introducing the jet of particle-laden gas into the jet relaxation region 38 where the particle velocities decrease substantially, as already explained, and the charged particles are delivered to an electrostatic gate region 54 configured to trap and release charged particles into the drift region 46 of the drift tube 50. In the electrostatic gate region 54, three grids 56, 58, and 80 are disposed so as to control the flow of charged particles info the drift region 46. In addition, in the electrostatic gate region 54, a focusing electrode 62 is used to focus the particle flow toward the centerline of the apparatus 50. In order to illustrate the operation of the focusing electrode 82, an exemplary charged-particle trajectory 64 is illustrated in FIG. 4 comprising a portion 64*a* in the drift region 48, when the focusing electrode 62 is turned off, and a portion 64*b* with the focusing electrode 62 turned on. In the drift region 46, charged particles are separated according to their electrical mobility by maintaining an electric field by use of a plurality of ring electrodes 66. After flowing through the drift region 46, the particles finally pass through a detector grid 68 before impacting the metal detector 72. In one embodiment the metal detector 72 is made of a sintered material. The background gas exits through the metal detector 72. In another embodiment, the detector 72 is electrically isolated from a surrounding sintered metal element so as to allow the background gas to flow uniformly through an exit wall 70 of the drift region 48. One of the purposes of the detector grid 68 is to minimize or eliminate the registering of a current signal at the detector 72 before the particles actually impact the detector 72. The low pressure inside the drift tube 50 is maintained by the application of a vacuum to the exit wall 70 of the drift tube 50.

As charged particles arrive at the detector, they are drawn into the porous metal material where they are collected by filtration and deposit their charge which passes to a current measuring electronic circuit. The particles have an arrival time distribution caused by their size distribution. Smaller particles arrive at the detector before larger ones. The charge delivered to the detector by the particles generates a varying current in the electronic circuit and the amplitude of the current as a function of arrival time can be used to determine particle size and particle concentration. The drift tube is designed to measure predominantly singly charged particles so that the magnitude of the defector current at any specific drift time is proportional to the number of particles of a specific size. Those familiar with the art of time-of-flight measurements will appreciate the mathematical relationship between particle charge, particle diameter, electric field intensity, particle velocity, and gas pressure, along with background gas velocity. The resulting detector signal is a time-varying current from which particle size distributions can be mathematically extracted.

Therefore, the jet relaxation section 38, the gate region 54, and the drift region 46 make up the drift tube 50. In operation, gas, a small number of neutral particles, and an appropriate number of charged particles are drawn into the drift tube via an inlet orifice by virtue of the reduced pressure inside of the drift tube 50. The in-flowing particle-laden gas results in the formation of an expanding jet. Gas conditions in the jet, i.e., gas velocity and pressure, are such as to carry the particle-laden gas towards the gate region 54. Initially, the particle-laden gas jet is confined closely to the centerline of the drift tube 50. After the gas travels a certain distance (e.g., about 30 cm for some embodiments), the jet relaxes and expands across the bore of the drift tube 50. Placement of the gate region 54 at a distance from the inlet orifice is selected so as to allow the charged particles to be stopped by the voltage applied to one of the grids 56, 58, 60 mounted perpendicularly to the longitudinal axis of the drift tube 50. If the grids 56, 58, 60 are mounted too close to the inlet orifice, the gas velocity will be higher and will push particles through the grids even when high voltage is applied to them. If the grids are mounted farther downstream, the jet may have expanded to the wall of the drift tube 50 and a fraction of the particles will become lost to the wall or fail to reach the detector. In some embodiments, the grids 56, 58, 60 are screens extending across the entire cross-sectional area of the tube at the axial location where each is disposed. In some embodiments, only one grid is used. In another, two grids are used. Also, although three grids are illustrated in FIG. 4, that number should not limit the subject matter disclosed, i.e., embodiments using four or more grids are within the scope of the materials disclosed herein. In some embodiments the grids are wire screens. In some embodiments, an optimal location for the gate region 54 of the drift tube 50 may be obtained by use of computational-Fluid-Dynamics, or CFD, calculations of the gas dynamics, and a statistical diffusion simulation of the particles, as further summarized herein below.

In embodiments using three grids at the gate region 54, the drift tube 50 may be operated in three different modes, i.e.: (1) a blocking mode configured to prevent charged particles from entering the drift region 46; (2) a trapping mode, configured to accumulate charged particles in the region around the gate region 54; and (3) an injection mode configured to inject a burst of charged particles into the drift region 46.

The blocking operating mode is configured to prevent most particles from entering the drift region 46 for a period of time during which the background gas sweeps particles already in the drift region 46 towards the exit. This action improves the response of the detector 72 by eliminating or minimizing background signals. In this mode, the grids 58 and 60 are powered at blocking potentials while the grid 56 shields incoming particles from the electric field produced by the grid 58.

In the trapping operating mode, a stopping potential is applied to grid 60 and a lower trapping potential is applied to grid 58, while grid 56 shields the incoming charged particles from the potential applied to grid 58. The trapping condition creates an electrostatic potential valley perpendicular to the bore of the drift tube 50 in which charged particles are trapped. This condition provides a way to accumulate a substantial number of charged particles in the gate region 54 so that when they are eventually injected into the drift section 46, a larger detector signal is obtained, thus increasing the resolution and accuracy of the final measurement while reducing the time required for each measurement.

The injection mode starts by switching the potential applied to grid 58 and focusing electrode 62 during the accumulation mode to values higher than that applied to the grid 60. This raises the trapped particles to a potential that allows them to roll down a "potential hill" in the electric field inside the drift region 46 in the direction of the detector. It also blocks charged particles from entering the drift region 46 while the injected particles are rolling down the "potential hill."

In some embodiments, electric fields are established in the drift tube by means of ring electrodes and ring electrodes equipped with a fine mesh grid. The ring electrodes in the drift region are fabricated from stainless steel. A fine mesh grid having an open area of 85 percent is attached to a supporting ring electrode. The combination of a ring electrode and a fine mesh grid is a grid electrode. Practitioners in the art of fabricating mass spectrometers will appreciate the care needed to prevent electrical discharge from high voltage electrodes that are operated in a reduced pressure environment. The edges of the ring electrodes were polished to remove burrs and thus minimize the possibility of electrostatic discharge from burrs. The grid electrodes and ring electrodes are separated from each other in the drift region and trapping region by means of dielectric spacers. In some embodiments, electrical contact between a high voltage power supply and each ring electrode or grid electrode was accomplished by pressing a 1/16" diameter metal rod through a plastic tube fitting (1/8" NPT pipe thread×1/16" compression fitting) that was mounted externally on a radius of the insulating cylinder that surrounded the drift region. The bore of the tube fitting was aligned with the outer edge of a ring electrode. Electrical contact between the rod and a ring electrode was secured by friction and the opposite end of the rod was attached to a high voltage power supply by means of a corona ball. The corona ball was machined with internally threaded passages that accommodated set screws and served as a mechanical fixture for connecting the rod to a wire leading to the power supply and furthermore provided a way to minimize corona discharge by covering the sharp edges of the wire and the rod.

Figure 5A:
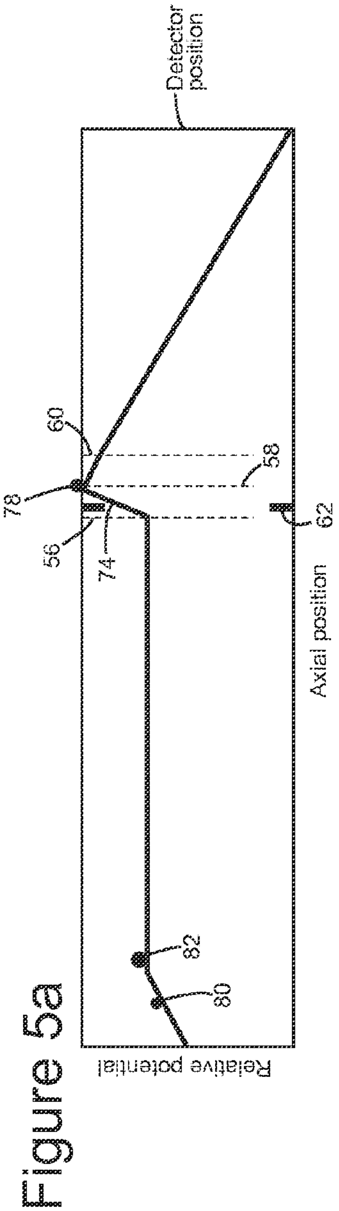
FIGS. 5A-5C illustrate yet another drift tube according to yet another exemplary embodiment of the subject matter disclosed.
Figure 5B:
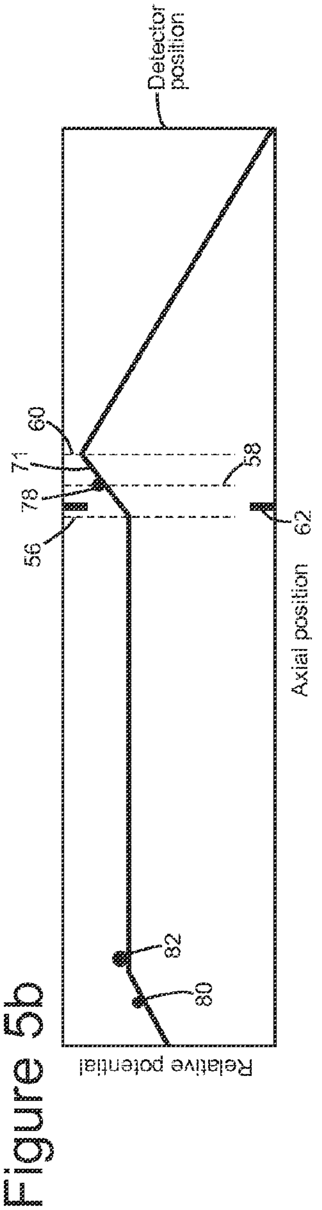
Figure 5C:
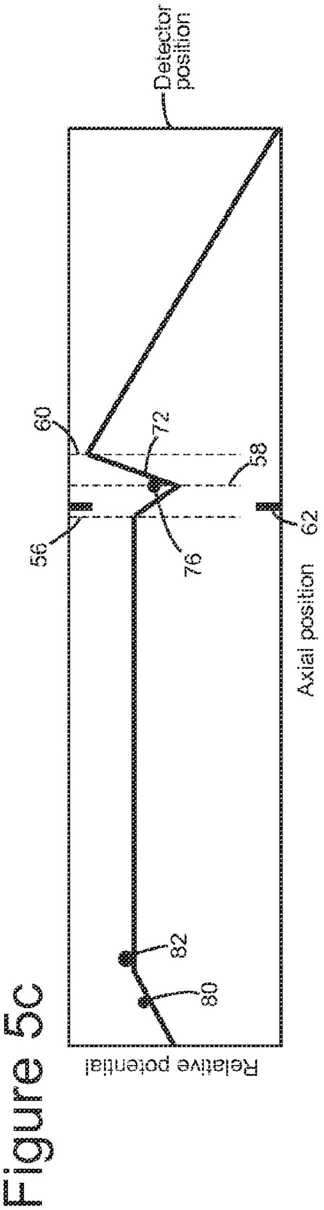

A representation of the axial variation of the relative electric potentials in a drift tube according to one embodiment of the subject matter disclosed for the three modes of operation of the electronic gate disposed in the electrode gate region 54, as just explained, is presented in FIG. 5. Voltages applied to the grid electrodes are switched depending on the mode of operation while the voltages applied to the tube electrode 55 and the ring electrodes 66 (see FIG. 4) may not necessarily be switched. In the jet relaxation region 38, a substantially constant potential is maintained in all three modes of operation by the tube electrode 55. In all three modes, the tube electrode 55 and the grid 56 remain at a constant potential. The shape of the electric field in the gate region 54 during the accumulation mode is illustrated by line 71 (FIG. 5B), the trapping mode is represented by line 73 (FIG. 5C), and the injection mode is shown by line 74 (FIG. 5A). Particle 76 represents a particle trapped in the electrode gate region 54. Particle 78 represents a trapped particle whose potential has been elevated to a high level and is free to roll down the potential hill towards the detector located at the bottom of the hill. Positively charged particles will roll down the potential hill, but negatively charged particles will remain at the top of the hill. Around the particle inlet location, there is an increase in the electrical potential by keeping the nozzle grounded as to control the size of particles that will actually enter the drift tube. In FIG. 5, particles 80 and 82 represent incoming particles of different sizes. As shown, small particles 80 fail to rise up the up-potential while larger particles 82 are pushed up the hill by the gas jet. This up-potential feature excludes small charged particles from entering the drift tube and serves to improve detector sensitivity for nano-particles. As already explained, the focusing electrode 62 is located between the grid 56 and the grid 58. It is switched and operated at intermediate voltages so as to prevent the particles from diffusing radially so as to avoid detection when flowing past the detector 72.

In the drift region 46 charged particles are exposed to a fixed electric field generated by maintaining an approximately constant voltage drop between each electrode, thus the electric field is constant along the bore of the drift region. This means that regardless of where particles are located radially or longitudinally, they will experience a well-defined electric force that moves positively charge particles towards the detector. The profile of the gas velocity in this section is nearly flat, but not perfectly flat, and this imperfection contributes to a variation in particle velocity across the diameter of the drift region. Knowledge of the background gas flow field, as obtained from CFD calculations, allows this variation to be remedied by means of mathematical algorithms, i.e., deconvolution of the arrival time distribution signal, as further explained below.

The detector is preceded by a grounded grid (the detector grid 68 shown in FIG. 4) that prevents arriving charged particles from creating a detector signal before they actually hit the detector 72. In one embodiment, the detector is a disk of a porous sintered electrically conducting metal. A portion of the carrier gas is withdrawn through this disk, which serves to filter out the charged particles. As the charged particles are collected in the porous material of the disk, their charge is detected as a current. The varying current signal is then converted mathematically to an arrival time distribution and results in a spectrum of particle sizes. The determination of size is a straightforward derivation based on the operating conditions in the drift tube. Basically, time slices in the observed time history of the signal observed at the detector can be converted to particle size. The conversion can be derived from first principles or by calibration.

In addition, as previously explained, when voltage is applied to the focusing electrode 62, charged particles are focused towards the center of the bore of the drift tube 50 as shown by the particle trajectory 64*b* in FIG. 4. The focusing effect serves to work in opposition to the gas jet which causes particles to diverge from the centerline of the drift tube. When voltage is not applied to the focusing ring electrode 62, particles follow gas streamlines, one of which is depicted by the particle trajectory 64*a*. As illustrated, the particle trajectory 64*a* terminates at the exit 70 of the drift tube 50 at a radial position that misses the porous detector disk 72, thus this particle escapes detection. The focusing effect serves to guide more particles onto the detector disk 72 and improves detection efficiency. In a second embodiment, the focusing electrode 62 is replaced with a hemispherically shaped fine wire mesh grid positioned in a manner such that the approaching charged particles pass from the outside of the hemisphere, through the grid to the interior of the grid where they become focused towards the centerline of the drift region by the local electric field.

An up-potential hill is depicted in FIG. 5 near the jet inlet region. It begins at the inlet orifice and extends a short distance along the jet expansion section. The up-potential hill results from the voltage applied to the tube electrode 55 and the grounded inlet tube 52. The up-potential hill in 3D is an uphill valley. The valley serves to confine and focus charged particles near to the centerline of the bore of the drift tube. In certain embodiments the slope of the uphill may be optimized to preclude small charged particles from entering the drift tube. All gas-borne particles that pass through the inlet orifice experience a strong aerodynamic force—they are dragged by this force. Positively charged particles are subjected to a repulsive force created by the positive potential applied to the tube electrode 55. The repulsive force acts more strongly on small particles and prevents them from travelling up the potential hill. This design feature excludes small positive particles from entering the drift tube and serves to reduce a background signal at the detector. Small and large negatively charged particles will travel up the potential hill. Positively and negatively charged particles that reach the electrode gate region 54 will be trapped and accumulated, but only the positively charged ones will be injected into the drift section 46 of the drift tube. In another embodiment, voltage applied to the grid 56 can be adjusted for the purpose of excluding negatively charged particles from entering the gate. One example of this adjustment is to set the voltage applied to the grid 56 at a value smaller than the voltage applied to the inlet jet tube 52. The effect is to create a decreasing positive potential along the axis of the gate region which blocks some of the negatively charged particles and, at the same time, enhances the function of the focusing electrode 62.

Figure 6:
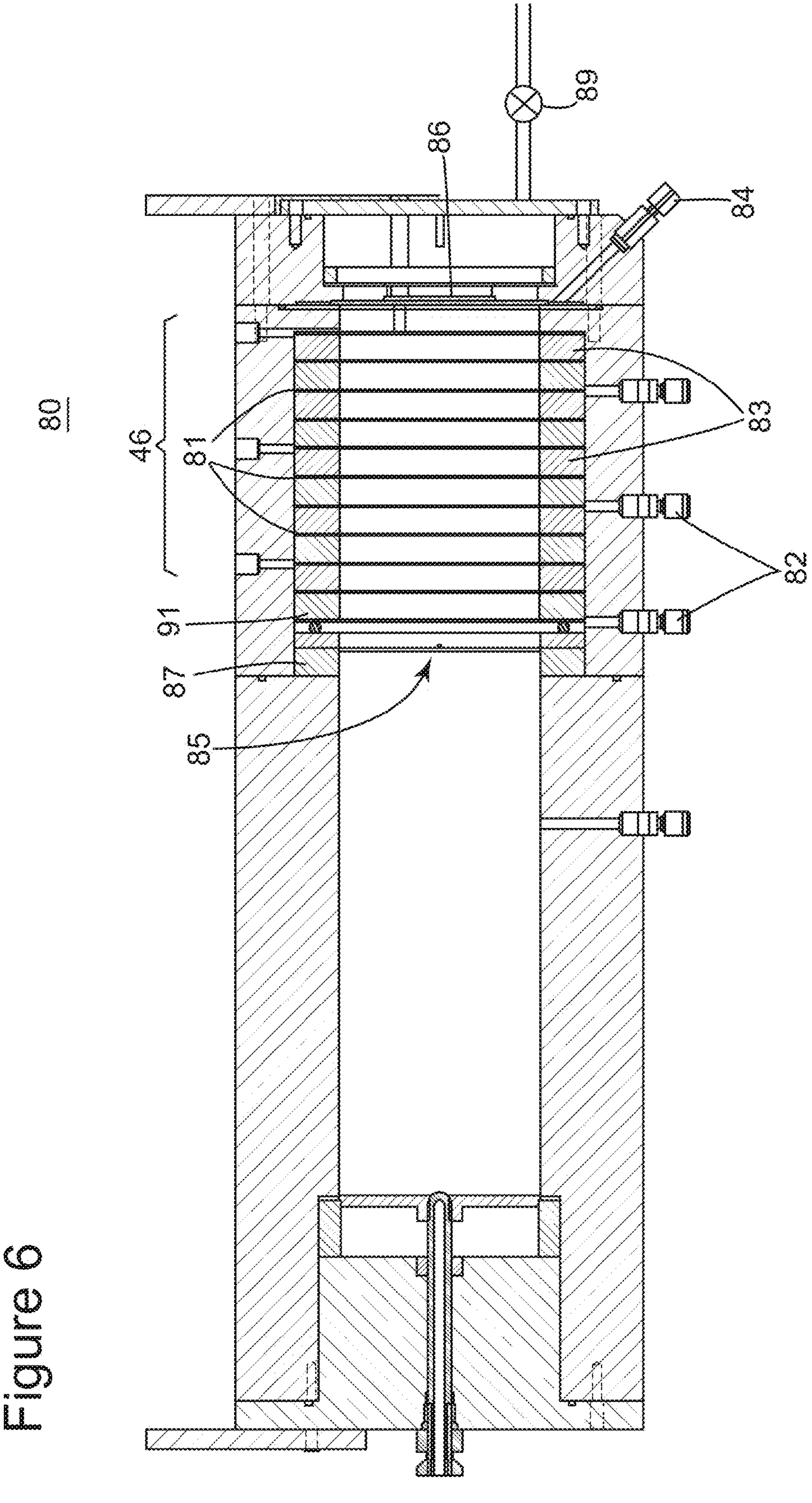
FIG. 6 illustrates yet another drift tube according to yet another exemplary embodiment of the subject matter disclosed.

Another exemplary embodiment of the subject matter disclosed is illustrated in the drift tube 80 of FIG. 6. In the exemplary embodiment shown, the electrodes 81 are comprised of a series of electrically conducting axially aligned disks having centered holes, connected in an arrangement where the disks are separated from each other by means of axially aligned dielectric disks 83, also with centered holes, this series being sealed together in an arrangement forming a tube capable of conducting a flow of gas. In addition, the entrance to the drift region 46 is connected to the electrode gate by a dielectric spacer 91 and the exit of the drift region is connected to a vacuum pump (not shown) configured to lower the operating pressure of the drift tube to desired levels as previously explained. In this exemplary embodiment the bi-functional electrode gate 85 also comprises electrically conducting grids or screens, the electrode gate 85 being attached to the end of the jet relaxation region by use of dielectric spacer rings 87. In addition, the drift tube 80 further includes a power supply (not shown) connected to the electrode gate 85 configured to power the grids or screens with either a static or pulsed voltage. In one embodiment, the voltage supplied to the grids is pulsed so as to cycle through the various operational modes of the electrode gate, previously explained. Those of ordinary skill will appreciated the fact that care should be exercised to reduce electrophonics.

In the embodiment shown in FIG. 6 the detector 86 comprises a metal place connected to the end of the drift tube region by use of a dielectric spacer ring and the current generated by the charged particles impacting the detector 86 are measured by use of an ammeter connected to the porous disk electrode, which in turn is connected to an ammeter. In addition, the drift tube 80 also includes a recording device (not shown in FIG. 6) configured to register or record the magnitude of the ammeter signal when a pulsed voltage is applied to the electrode gate and continues recording until the majority of particles gated into the drift region or second chamber strike the detector plate 86.

Figure 7:
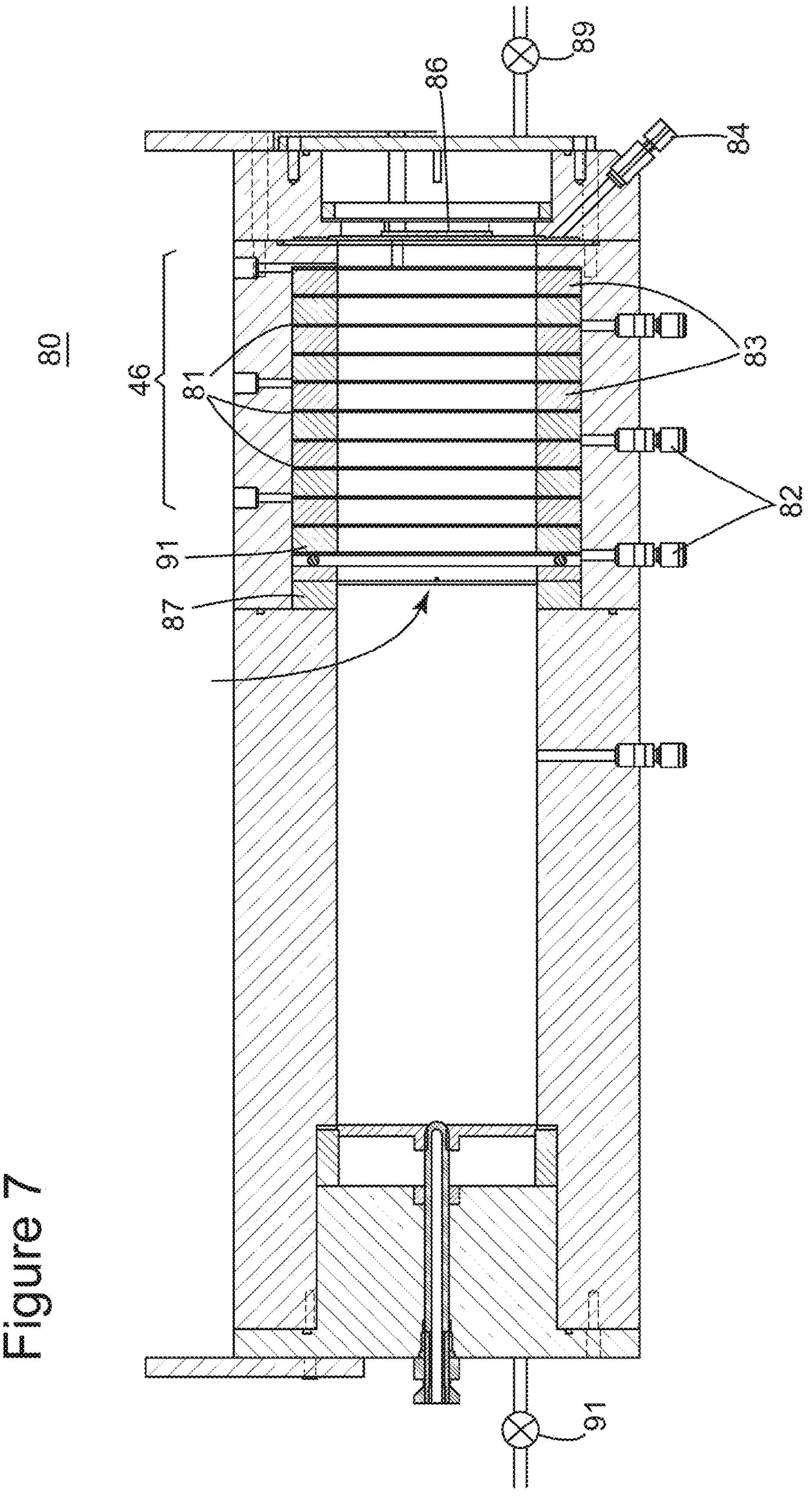
FIG. 7 illustrates yet another drift tube according to yet another exemplary embodiment of the subject matter disclosed.

In the embodiment illustrated, one or more valves 89 may also be provided so as to control the background gas flow during operation of the drift tube 80. In operation, after charged particles are accumulated in the gate region, the valve 89 is dosed so as to momentarily stop the flow of background gas in order to minimize the effect of that variable on the measurement. Once the measurement is finished, the valve 89 is opened and the gas flow starts again. In another embodiment, a second valve 91 is installed at the inlet of the drift tube 80, as shown in FIG. 7. In operation, after the particle trap is appropriately filed with charged particles, the valves can be dosed so that the drift tube can be operated with static gas—no flow, while maintaining particles in the trap. Then the trapped particles may be released into a stagnant gas. This will increase performance because any influence of gas eddies will be removed. In another embodiment, it is also possible to trap charged particles in the electrode gate and then introduce a counter-current flow of clean gas from the exit end, so as to flush out solvent vapors that were carried initially into the drift tube along with particles before making the measurements. In some of the embodiments including these valves, once the flow of clean gas is introduced, both valves can be dosed and measurements made under static gas conditions. Subsequently, the drift tube operates normally with both valves open. In some embodiments these valves are electric valves. The timing of the operation of these valves may be varied to accomplish the described effect on the background gas flow.

After evaluation of the subject matter disclosed herein, those of ordinary skill in the applicable arts will appreciate the existence of many variations and equivalent embodiments and associated methods and systems to be discussed further later. For example, the background gas could be introduced ‘backwards’ through the porous detector plate and/or through the secondary porous wall surrounding the detector. Such embodiments would be advantageous at least in part due to optimized operating conditions for small molecules when solvent vapor might degrade performance. In other embodiments, the electrode gate could be designed to focus charged particles more severely before they are released by a 2-stage voltage switching protocol, thus such a focusing could then be designed to minimize the influence of counter-current gas flow and prevent charged particles from being blown backwards up the trapping region. In other embodiments, the counter-flow gas could be a reactive gas that is used to identify specific charged particles due to a shift in drift time that corresponds to an adducted species of charged particles. In yet other embodiments, elimination of the reactive charged particle pulse due to the co-transport of negatively charged particles being electrostatically dragged along by positively charged particles would be advantageous. Also, operation in negative polarity modes would be desirable in some embodiments because some materials such as DNA are more readily charged with a negative charge. Finally, the embodiments explained here to prepare and deliver charged particles to the drift region so as to allow the measurement of their size and concentration could also be used for other purposes. For example, the first chamber containing the relaxation region and the electrode gate may be used to hold charged particles for secondary purposes, such as to generate an e-beam to alter charge states; to illuminate the accumulated charged particles with a free electron laser (FEL) for coherent x-ray diffraction; to measure the fluorescence properties of the trapped particles; or to hold them for release into a mass spectrometer.

It has been reported in the literature that some molecules change shape (conformation) in concordance with the level of charge they carry. It is useful in some studies to alter the charge state of trapped molecules for the purpose of measuring their cross section as a function of the number of charges they carry. This information may be used to investigate the stability of individual molecules or the stability of molecular clusters. Fluorescence measurements of trapped molecules could be used for example as a way to measure the efficiency of chemical derivatization reactions that are commonly used to label protein molecules. Coherent x-ray diffraction provides 3-D information about a molecule's structure. The present way to perform coherent x-ray diffraction studies is to introduce a beam of nanocrystals or molecular complexes into a rapidly switched x-ray beam and collect diffracted photons before the x-rays explode the target molecule. Current technology consumes inordinate amounts of carefully isolated molecules. By trapping the molecules in the drift tube and releasing them synchronously with the pulsed x-ray laser it will be feasible to use samples more efficiently. Some forms of ion mobility have already been operated in combination with a mass spectrometer. The development of a charged particle mobility spectrometer, as described here, will further enable the study of molecular conformation with molecular identification by means of mass spectrometry.

Those of ordinary skill in the applicable arts will appreciate that the subject matter disclosed can be further broadened and/or optimized by the use of a mathematical model of the applicable physical concepts, such as fluid flow, particle interactions with the flow of a gas, selection of operational voltage levels for the various electrodes disclosed and explained, etc. In the paragraphs that follow, a summary is presented of the modeling analysis performed by the inventors to further investigate the many benefits of the subject matter disclosed by use of a combination of simple analytical relationships that guided the general concepts, followed by detailed flow calculations using a CFD commercially available software. The applicable analytical equations provided general functional dependencies on the important parameters, while the CFD software identified the detailed influence of turbulence, flow recirculation, gas velocity and pressure within a drift tube. Furthermore, by use of user-defined functions, the CFD software was further modified to include the simulation of an electrical field and particle dispersion and/or behavior in order to simulate charged-particle motion, gas and particle trajectories, and travel time caused by the gas flow and electric fields.

Based on the values of the Reynolds numbers, or $Re_d$, applicable to the drift tubes disclosed herein, the CFD software was configured to simulate turbulent flow conditions based on values of tube diameter, jet exit velocities, and kinematic gas viscosities. Two different turbulence models were tested. Velocity contour plots generated using k-$\epsilon$ and S-A turbulence models gave similar results, indicating that the particular choice of turbulence model was not critical. Because the k-$\epsilon$ model is the most general viscous model used in fluid dynamics and simulates viscous effects better than the S-A model, the calculations for particle trajectory carried out in the CFD code were all based on the k-$\epsilon$ model.

Initial model calculations performed direct flow calculations without consideration for particle effects. Following confirmation of a feasible jet flow, particles were then seeded into the gas flow calculations with an electric field and the resulting motion of singly charged particles was modeled. Given the required number of charged particles for feasible measurements, particle concentrations are low, and thus do not affect the gas-phase flow. In addition, the particles are small and follow the primary flow field because equilibration times with the flow for 20 nm particles at 0.1 atm are less than a microsecond.

Small particle slip was modeled considering values of the Knudsen numbers, or Kn, which characterizes the relationship between gas phase and particle flow based on particle diameter, mean free path of gas phase molecules, and pressure. For small particles and low pressures, Kn is large, on the order of 100 or greater, which suggests the use of a correction factor (Cunningham, Cc), when particle trajectories are calculated. For the small particles modeled in the drift tube, they generally follow the primary gas jet, although they have sufficient momentum to avoid recirculation as discussed below. This can be shown to be true by consideration of a characteristic stopping distance, i.e., the distance that the particles would traverse if injected into a static environment with an initial velocity $V_o$. Conversely, the stopping distance can also be viewed as a "starting" distance to accelerate a particle to a final drift velocity. It has been shown that about five stopping distances are required for a particle to equilibrate within 1% of the gas velocity. For small particles at low pressures, characteristic stopping times are small (<1 μs), and thus the particles (in the absence of an electric field) tend to follow the flow very closely. For example, the corresponding stopping distance for $V_o$ equal to 10 m/s is only about 1.4 μm. Thus particles equilibrate with the gas phase flow very quickly. There is a small velocity lag at the initial highest velocities, but microsecond lag times are small compared to total residence times in the jet of 25 ms. Particle drift velocities that may be present when a particle is accelerated in an electric field can also be modeled by taking into consideration a terminal steady state velocity of the particles in a given electric field, resulting in an equation for a total drift time that depends only on the background gas velocity, drift velocity, and the length of the drift tube. Finally, the effects of diffusion during the drift period can lead to a wider packet of particles, reducing time resolution. In addition, during the gate collection period, diffusion can contribute to radial spread if electric field confinement is not used. This effect has been taken into account by considering a RMS diffusion distance over the drift tube length, resulting in a conclusion that the irreducible diffusion broadening of a drift tube is independent of particle size, and only dependent on the electric field and drift tube length; variables that are relevant in defining the resolution limits of the instrument. In practice, the ratio of drift velocities to background flow velocity is more important in determining the resolution for the largest particles. Singly charged smaller molecules travel faster in the drift tube and therefore have a shorter time to diffuse, while larger ones travel more slowly, but since their diffusion velocity is also smaller, the two end up diffusing about the same distance as they fly through a fixed-length drift tube.

Figure 8:
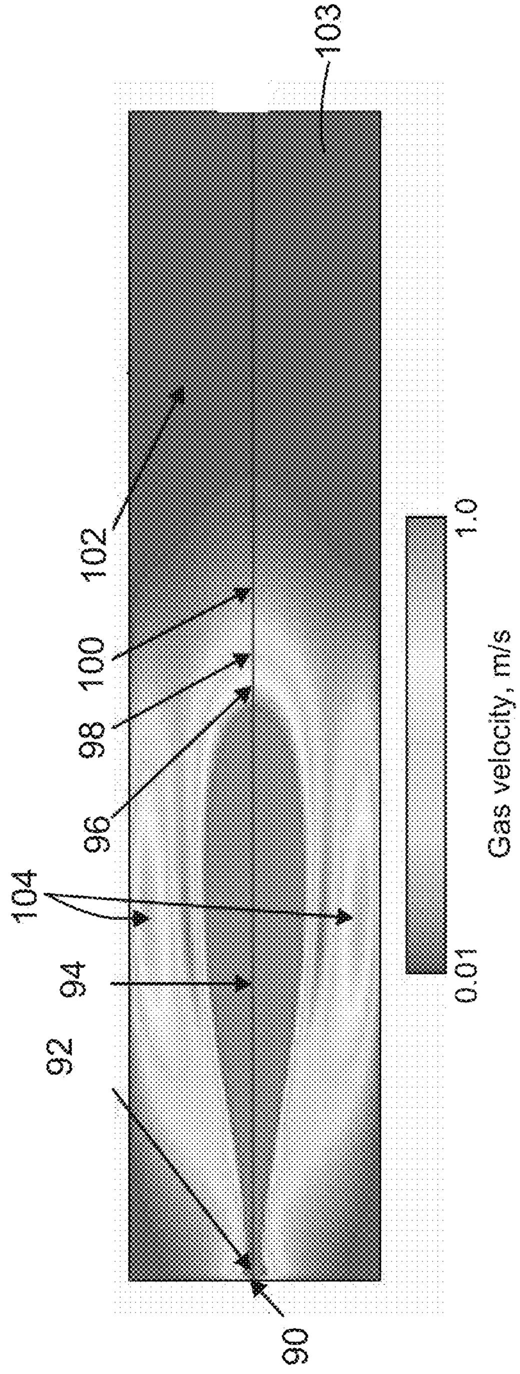
FIG. 8 illustrates an exemplary velocity contour map of a jet flow for a drift tube according to one embodiment of the subject matter disclosed.

FIG. 8 illustrates an exemplary velocity contour map of a jet flow for a drift tube obtained by the CFD model as just explained. At the bottom of FIG. 8, a gray scale is included to illustrate the velocity magnitudes illustrated in the figure. The primary features of this figure show the higher velocity core of the jet 94 (for all velocities >1 m/s), followed by a low velocity region 102 at the exit. The nozzle transmits particle-laden gas from atmospheric pressure into the drift tube. The exit of the drift tube, on the far right, maintains uniform flow at the assumed operating pressure (0.1-0.01 bar), resulting in choked flow (sonic velocity) at the jet nozzle and Poiseuille flow at the exit. While there are gas-phase recirculation cells 104, particles remain confined to the central core of the jet until reaching the low and uniform velocity region at the drift tube exit. The predictions illustrated in FIG. 8 allowed determination of the optimal gate location, where the gas velocity relaxes to an acceptable velocity (<1 m/s). Other features illustrated in FIG. 8 include: the entrance orifice at 90, the incoming jet of gas at 92, a region of velocities greater than 1 m/s at 96, a region of lower gas velocity in the range of 0.9-0.8 m/s at 98, a region of medium gas velocity at 100, a region of recirculating gas at 104, and the exit of the drift tube at 103.

Figure 9:
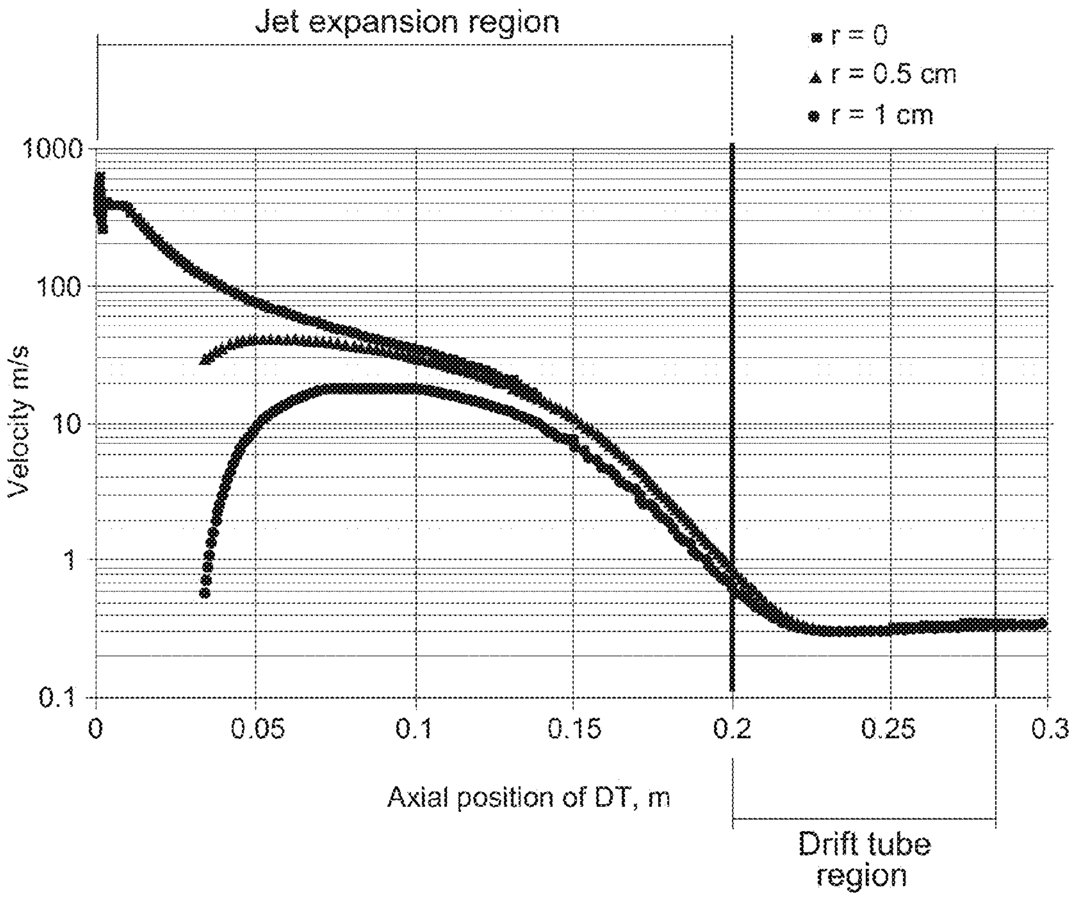
FIG. 9 illustrates an exemplary variation of jet velocity as a function of axial location for a drift tube according to one embodiment of the subject matter disclosed.

FIG. 9 illustrates more quantitative details of the CFD calculations and shows the jet axial velocity profiles at several radial positions, all relative to the gate, drift tube, and detector positions. There is a rapid decrease in flow velocity below supersonic speeds in the first few millimeters, followed by a jet expansion of approximately 15-degrees-included flow cone. In the near region of the entrance wall, low velocity recirculation eddies will form. CFD computations show that the small particles (<200 nm) equilibrate with the local gas flow velocity very quickly (with microseconds), and remain very close to the centerline (<5 degree included expansion cone). The result for the conditions simulated here is that the particle trajectories stay within a 0.8-cm radius until an axial position of about 20 cm, where the axial velocity has slowed to less than 1 m/s. As can be seen in FIG. 9, the axial flow velocity profiles following the gate position (20 cm) are all nominally similar downstream of that axial position.

In order to evaluate the extent to which the gas flow influences particle trajectories the dispersion of one hundred 20-nm-diameter particles was simulated by computationally releasing them across the jet orifice and using the same expanding jet conditions shown in FIG. 9. The CFD code determined the paths followed by these particles as they traveled through the drift tube. The simulation results showed that the initial high velocity momentum of the particles confines the particles to the center of the jet as described above. The particles remain close to the centerline of the drift tube until they travel about 15 to 20 cm axially (penetration distance depends on total mass flow), at which point they acquire a larger radial velocity component and the beam expands more substantially as the jet collapses and the gas jet slows and expands to fill the drift tube cross-section. For all these computations, validity is confirmed by overall conservation of mass flow combined with numerical convergence between CFD results and results calculated with analytic expressions.

The simulated particle trajectories show that it is feasible to install an electrostatic gate, for stopping and releasing particles, for the purpose of making time-of-flight particle electrical mobility measurements. The particle trajectory calculations show that there is an optimal gate location, where the velocity across the jet radius is nearly uniform, yet the particle jet radius has not over-expanded into lower particle velocity regions.

Following a gate accumulation period from about 0.5 to about 10 seconds (to increase signal levels), but not limited to this time range, particles are released into the uniform electric field drift region, where particles become separated in time and space according to their diameter. This behavior is simulated in the CFD model, again by gating one hundred 20-nm-diameter singly charged particles into the expanding jet at a location where the local flow velocity, in absence of an electric field, is approximately 1 m/s. A uniform electric field in the range of 1 kV/cm is also introduced into the model. Because the particles are confined closely to the centerline, it is assumed that a practical drift-tube electric field will be nearly uniform along the longitudinal-axis. The results of this calculation now represent the behavior of charged particles in the flow field combined with the electric field drift velocities, i.e., the performance of a classical drift tube.

Using the results of the CFD computations, one can compute the variation in TOF to the detector by two different methods. The first method is to compute directly, using the CFD code, the variation in TOF for each particle size. A second simpler and more flexible method is to use the variation in axial velocity profiles (as a function of radius), to compute the variation in TOF by computing the sum of background flow velocity and drift velocity as a function of size. The latter method allows decoupling of the TOF computation from the CFD calculations, once an optimal geometry for the jet flow has been determined, using two axial velocity profiles at the centerline and maximum radius to determine the maximum variation in TOF.

Figure 10:
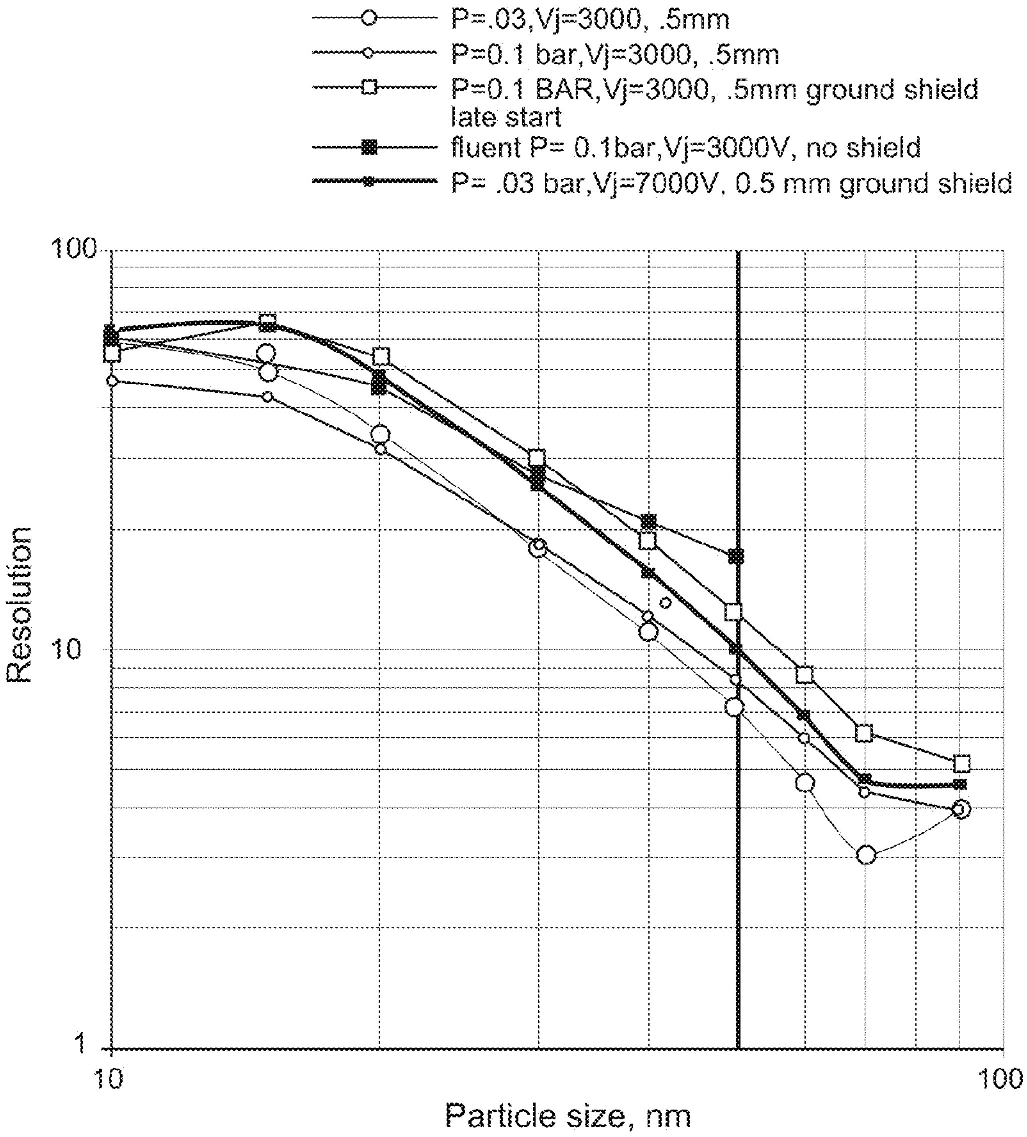
FIG. 10 illustrates a variation of resolution as a function of particle size for various operating pressures, jet flowrate, and voltage parameters for a drift tube according to an exemplary embodiment of the subject matter disclosed.

One of the conventional methods of characterizing drift tube performance is to optionally specify a minimum size resolution based on the maximum observed variation in TOF. In practice, the resolution based on standard deviation of the time-of-flight signal may be a factor of two better, so this minimum size resolution is a conservative estimate of performance. FIG. 10 shows the results of estimates of the minimum size resolution at various drift tube pressures and voltages, showing that the resolution decreases with increasing particle size because the ratio of drift velocity to background flow velocity decreases with increasing particle size. As a result, the variation in background flow velocity becomes a more significant factor for resolution degradation as particle size increases. For applications involving lipoprotein particles, the requirements for resolution are important at 20 nm, where calculations show the best performance. Most of the results of FIG. 10 were based on using the CFD velocity profiles combined with an analytical formula, but one case was performed directly with CFD, showing good agreement with the analytical estimates.

One parameter of choice of drift tube voltages, discussed in more detail below in the section on electrostatics, is the Paschen limit for corona discharge, which must be avoided. The Paschen limit predicts an upper limit for establishing an electric field without electrical discharge for a range of operating pressures. The selection of voltage parameters for the gate and drift region are chosen so as not to exceed the Paschen limit. In general, there appears to be improvement in resolution by operating at the highest possible voltage for a given pressure.

As understood by those of ordinary skill, there may exist additional fundamental and practical sources of resolution degradation. One fundamental limit is based on diffusion during the drift time. Simulations carried out for an electric field of 1000V/cm, and a drift tube length of 10 cm indicated that diffusion appears to be negligible for particles in the lipoprotein size range. In addition, there is a limitation given by the physical width of the potential valley in which particles are trapped, relative to the total length of the drift tube, which provides a significantly better estimate of resolution compared to the more deleterious effects of variation in background flow velocity. An overall resolution of the system may be given by incorporating the effects of diffusion, gate spread (width of trapped particle cloud), and jet background velocity variations. In this case, comparisons with current differential mobility methods give a maximum resolution value (1 sigma) value in the range of 25, decreasing with particle size and pressure, in sharp contrast to the subject matter disclosed.

In order to simulate the electric charges at the drift tube gate and electrodes commercially available software, Simion, along with a modified Statistical Diffusion Simulation (SDS) Model was used to evaluate a number of different designs for the gate electrodes and the electrodes in the drift region. Simion calculates the shape of the electric field around electrodes and the SDS Model calculates the motion of charged particles as they diffuse, or are dragged, through a reduced pressure gas under the influence of an electric field superimposed by Simion. The results of these calculations are particle trajectories and particle velocity at any location along a particle trajectory.

One way to present the result of the Simion and SDS calculations is to plot particle trajectories superimposed on a potential energy surface. A simple way to think of the potential energy surface is to consider the path of a golf ball on a putting green. A charged particle responds to the shape of the potential energy surface in the drift tube similarly to the way a golf ball moves on a putting green—it goes downhill and moves away from hills.

Figure 11:
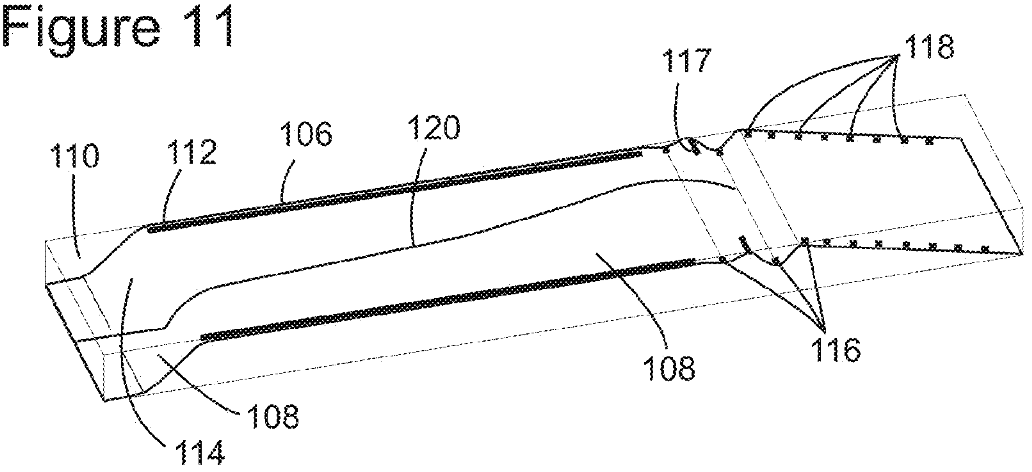
FIG. 11 illustrates an electrical potential surface for a fixed set of voltages applied to the electrodes of a drift tube according to an exemplary embodiment of the subject matter disclosed.

FIG. 11 shows the potential energy surface 108 of the drift tube for a fixed set of voltages applied to the electrodes in the drift tube. The height of the potential energy surface at any location is due to the magnitude of the local electric field—a stronger (higher) local electric field raises the local potential energy surface. The shape of the surface is a consequence of the voltage applied to the electrodes 118 in the drift tube. A charged particle placed anywhere on the potential energy surface will tend to move downhill. Simion calculates the shape of the potential energy surface and the SDS model superimposes the influence of gas velocity and diffusion. The local gas velocity cannot be visualized in FIG. 11, but the consequence of the gas velocity on particle motion can be deduced from the shape of the potential energy surface and the path taken by a particle. The potential energy surface in FIG. 11 was designed to conduct particles exiting the inlet nozzle towards a trap where they accumulate.

In FIG. 11, the following regions of interest are illustrated: a grounded entrance 110 to the drift tube: a metal tube 112 surrounding the jet expansion region at a specified voltage (e.g., 7 kV), having an exit in some embodiments that is a grid; a rising potential valley 114; three gate electrodes 116 (the first being a ring equipped with a grid, for example, at 7 kV). the second a focusing ring electrode (e.g., 8 kV) and the third is a ring equipped with a grid (for example, at 5 kV); and a plurality of ring electrodes 118 disposed in the drift region. Line 120 represents a particle trajectory that begins as a particle escapes from the inlet nozzle and rises through a potential valley. The particle rises through the potential valley because it is dragged by high velocity gas in the expanding jet. As previously mentioned, small particles rapidly equilibrate (<10 μs) to the velocity and electric force fields. The particle could not rise through the potential valley if the gas jet were removed. Conditions are chosen, voltages applied to electrodes along with gas velocity and gas pressure, so that particles larger than about 5 nm are conducted up through the potential valley, while particles smaller than a particular size (e.g. 5 nm) fail to navigate the valley. By designing the shape of the valley to exclude particles smaller than 5 nm, it is possible to exclude small air and solvent ions from entering the drift tube and interfering with the detection of particles, thereby improving detection sensitivity within the size class of interest.

As shown, the particle trajectory 120 deviates from the centerline of the jet due to the influence of the expanding jet and arrives at the first portion of the gate electrode 116 in the form of a fine mesh metal grid in some embodiments. After passing through this first portion of the gate electrode 116, the particle experiences the effect of a focusing electrode 117 that introduces a small potential ridge that turns the particle towards the center of the drift tube. The focusing electrode 117 serves to confine particles (not shown) near the center of the drift tube, as already explained. The particle then rolls down a potential hill where it is stopped by an abruptly rising potential upslope. The upslope defines a trapping condition that catches incoming particles and prevents them from travelling axially. Here particles are confined in a potential groove in which they can move only radially (as a result of diffusion), yet are also constrained radially by the influence of the focusing electrode's potential. The shape of the valley in the trapping region is another advantageous design feature in the operation of the drift tube. The trapping valley provides a way to accumulate particles exiting the nozzle and holds them in a groove that serves to line them up along a starting line. The sharpness of the potential groove, i.e., the narrowness of the starting line, enhances resolution of a TOF measurement because after release all particles begin their drift towards the detector at nearly the same position. The trapping valley can be disposed in several embodiments, including, for example (1) as described; (2) with two trapping grids for further focusing the particles on the starting line; (3) with one or two curved grids; or (4) a gridless design wherein the particles are trapped in an up-sloping potential valley.

Figure 12:
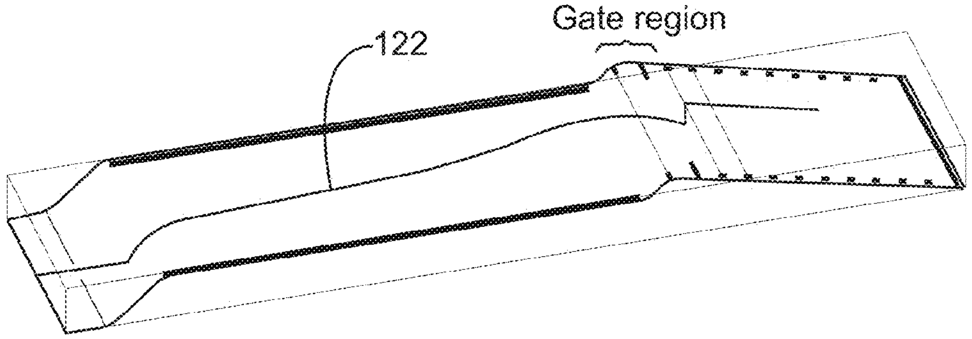
FIG. 12 illustrates another electrical potential surface for another fixed set of voltages applied to the electrodes of a drift tube according to an exemplary embodiment of the subject matter disclosed.

FIG. 12 illustrates a potential energy surface at the time the particles are released from the trap. The differences between FIGS. 11 and 12 occur in the gate region. The voltage applied to the first grid of the gate electrode 116, the focusing electrode 117 and the second grid of the gate electrode 116 are higher in FIG. 12 compared to FIG. 11. Raising these voltages creates a smooth flat downhill and allows the trapped particles to drift towards the detector at the end of the drift region. In FIG. 12, the steep vertical jump in the particle trajectory 122 describes the path taken by a particle sitting initially on the floor of the potential trapping valley, then elevated to the top of a potential hill by switching the voltages applied to the electrodes in the trap, and allowed to roll downhill.

After review of the subject matter disclosed herein, it will become apparent to one skilled in the applicable arts that many other embodiments with different shapes and numbers of grids and screens are within the scope of this disclosure. FIGS. 16-20 illustrate a few non-limiting examples of these embodiments. These figures illustrate various electrical potential surfaces for a given set of voltages applied to the various embodiments of the electrodes of a drift tube and the corresponding structural features of the grids to generate these electrical potentials.

Figure 19A:
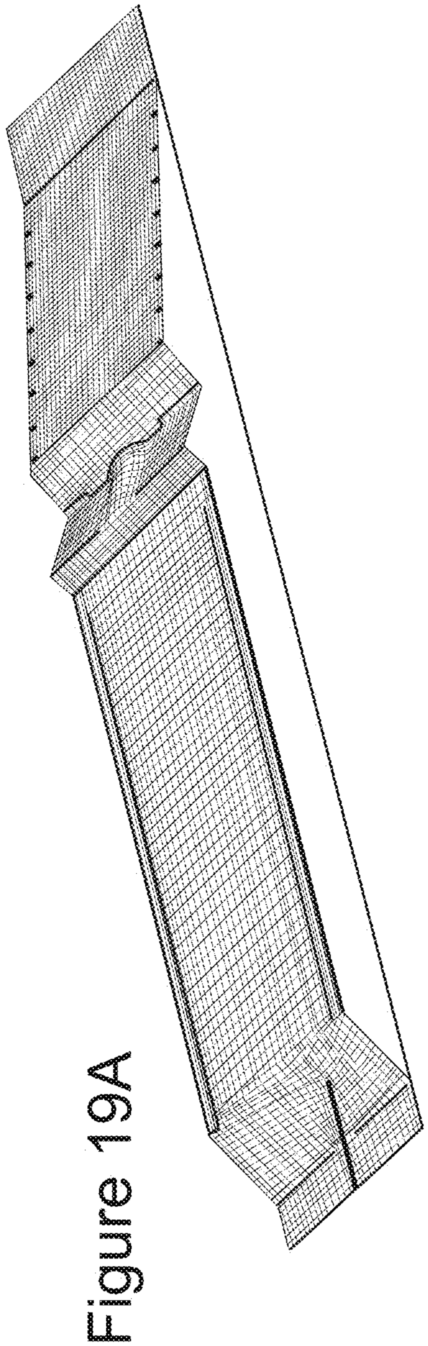
FIGS. 19A-19B illustrate an electrical potential surface for a fixed set of voltages applied to the electrodes of a drift tube (FIG. 19A) and the corresponding structural features (FIG. 19B) of the grids to generate the electrical potential illustrated in FIG. 19A according to an exemplary embodiment of the subject matter disclosed.
Figure 19B:
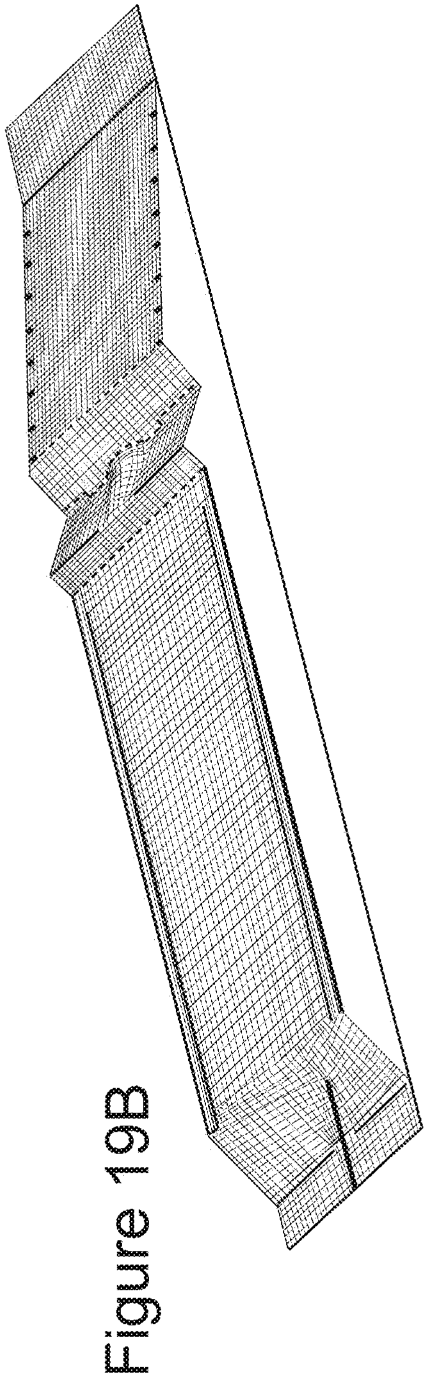

In FIG. 19, a second grid is configured in the shape of a hemispherical cap such that trapped charged particles in the spherical cap-shaped grid are prevented from migrating under the influence of a radial gas velocity component towards the wall of the drift section.

Figure 20A:
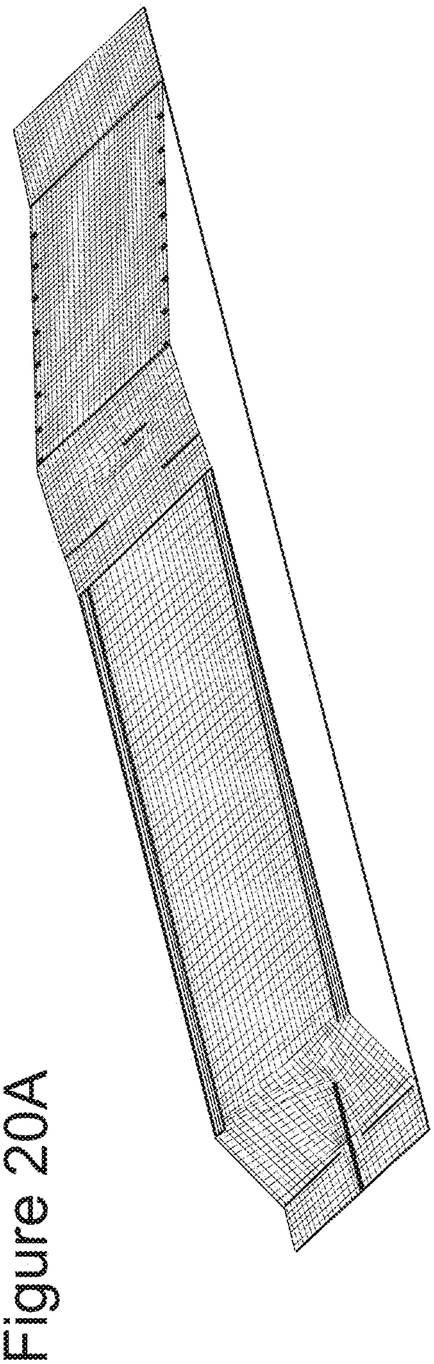
FIGS. 20A-20B illustrate an electrical potential surface for a fixed set of voltages applied to the electrodes of a drift tube (FIG. 20A) and the corresponding structural features (FIG. 20B) of the grids to generate the electrical potential illustrated in FIG. 20A according to an exemplary embodiment of the subject matter disclosed.
Figure 20B:
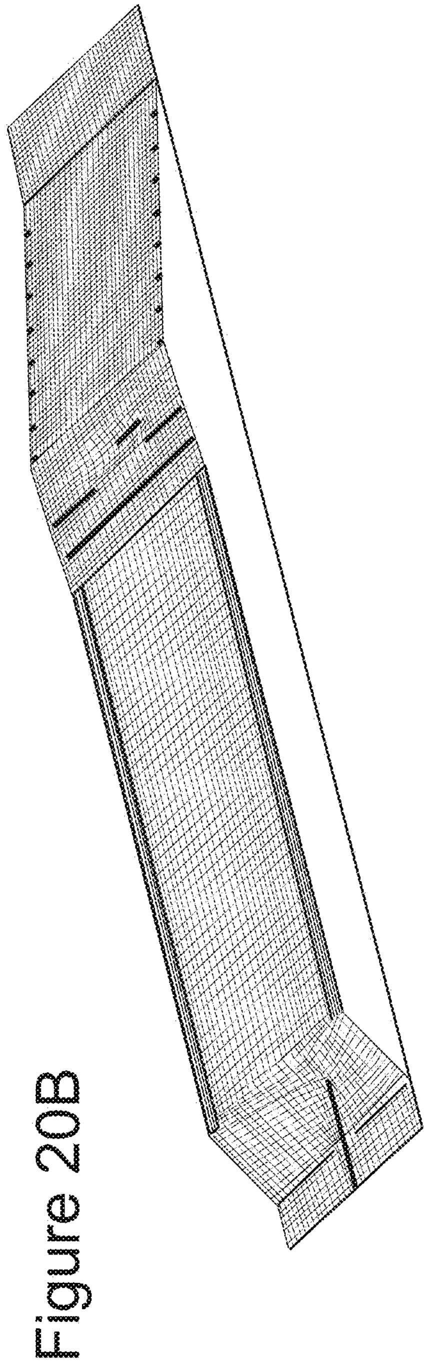

In FIG. 20, the trapping grid is a small diameter circle, the center of which is disposed on the centerline of the drift region by means of three or more fine support wires that extent to the inner diameter of a ring electrode. When configured with appropriate voltage, the small diameter grid creates a potential valley near the centerline of the drift tube and prevents charged particles from migrating under the influence of a radial gas velocity component.

Figure 16A:
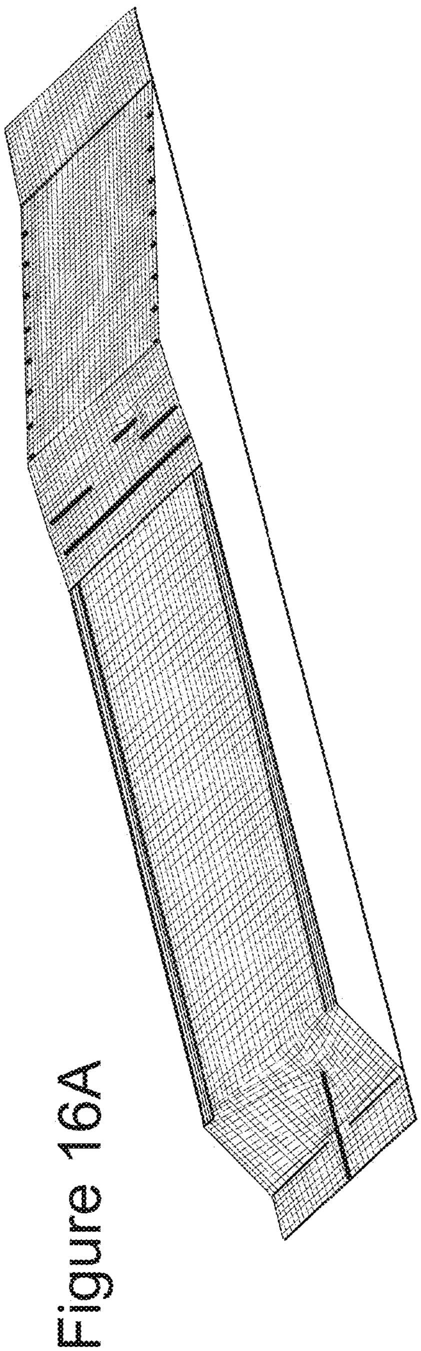
FIGS. 16A-16B illustrate an electrical potential surface for a fixed set of voltages applied to the electrodes of a drift tube (FIG. 16A) and the corresponding structural features (FIG. 16B) of the grids to generate the electrical potential illustrated in FIG. 16A according to an exemplary embodiment of the subject matter disclosed.
Figure 16B:
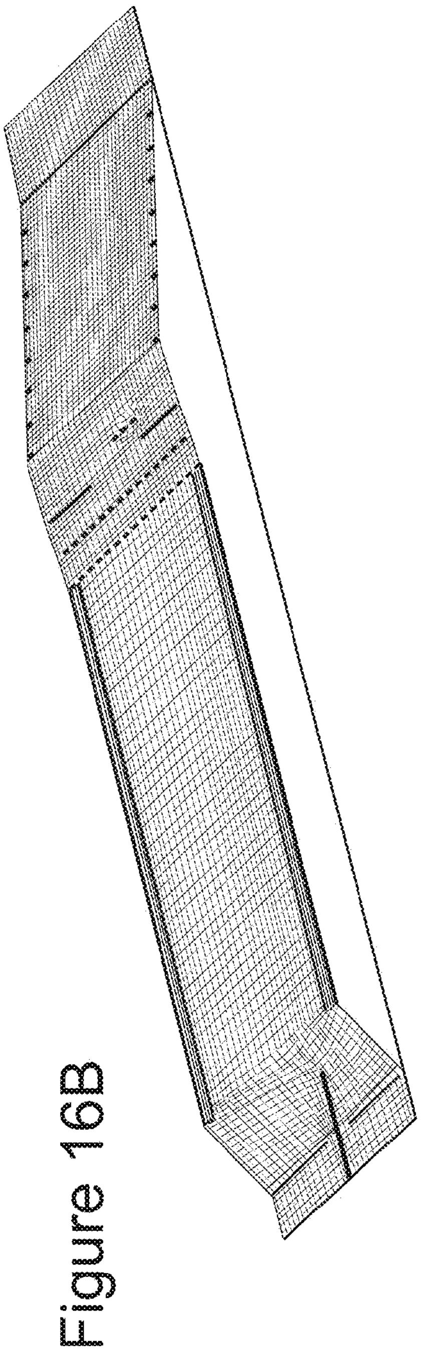
Figure 17A:
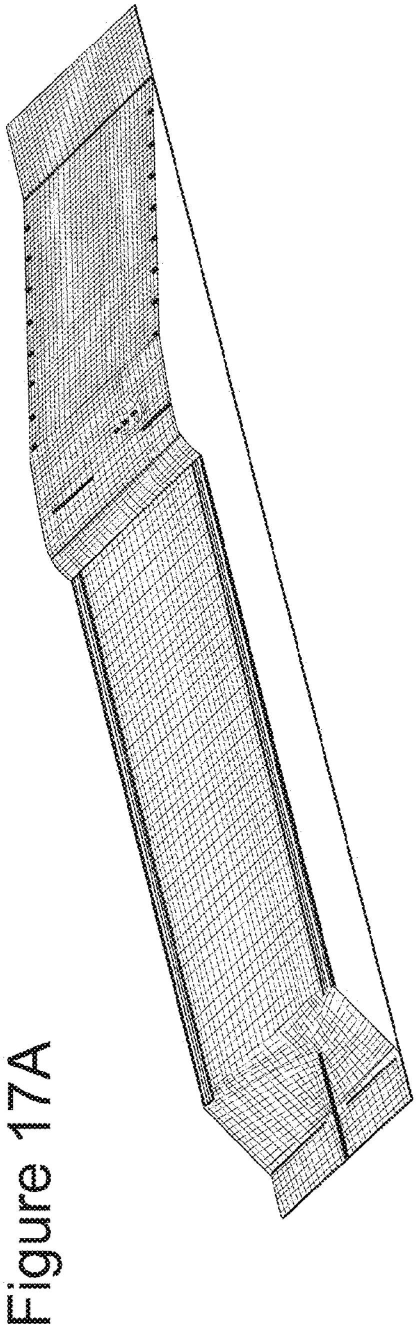
FIGS. 17A-17B illustrate an electrical potential surface for a fixed set of voltages applied to the electrodes of a drift tube (FIG. 17A) and the corresponding structural features (FIG. 17B) of the grids to generate the electrical potential illustrated in FIG. 17A according to an exemplary embodiment of the subject matter disclosed.
Figure 17B:
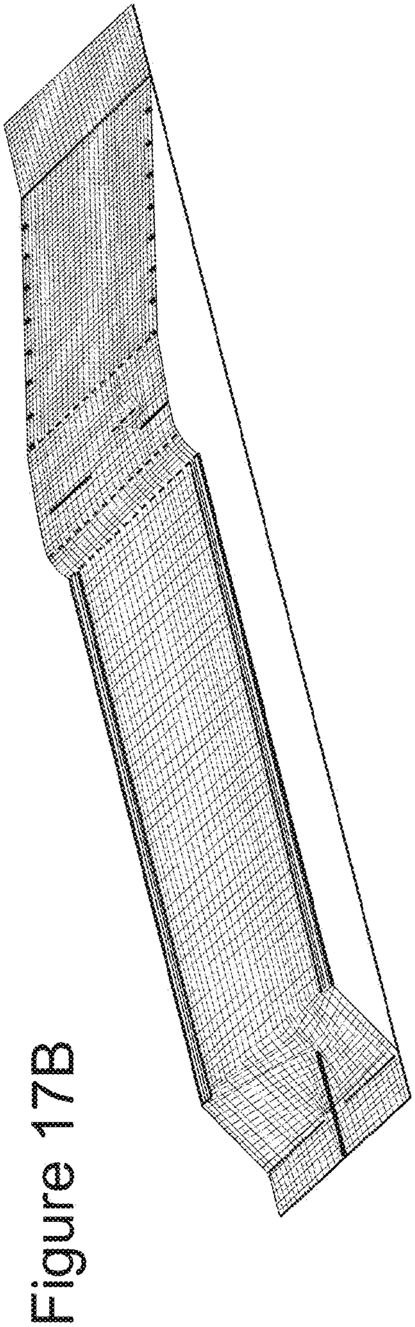

In FIG. 16, the exit end of the first chamber is equipped with a grid. The grid prevents an electric field generated by the first grid in the trapping region from entering the second portion of the first chamber. This embodiment efficiently blocks charged particles, due to the generation of a steep electric field between the grid attached to the exit end of the first chamber and the first grid in the trapping region, from entering the trapping region during the time trapped particles are released into the drift region. An exemplary embodiment of an electric field configured to produce such a result is presented in FIG. 16B wherein dashed lines are grid potential energy surface during trapping operation. When the exit of the first chamber is not equipped with a grid, as shown in FIG. 17A, the electric field generated by the first grid in the trapping region extends into the first chamber where a gradual up-slope potential surface results, as shown in FIG. 17B, which is less efficient for blocking charged particles from entering the trapping region during the time particles are released into the drift region.

Figure 18A:
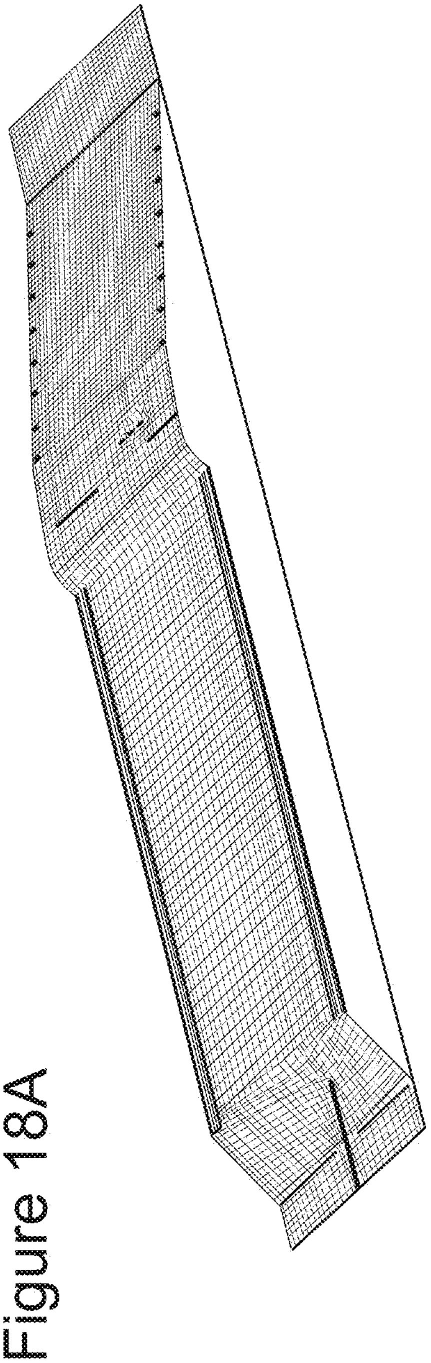
FIGS. 18A-18B illustrate an electrical potential surface for a fixed set of voltages applied to the electrodes of a drift tube (FIG. 18A) and the corresponding structural features (FIG. 18A) of the grids to generate the electrical potential illustrated in FIG. 18A according to an exemplary embodiment of the subject matter disclosed.
Figure 18B:
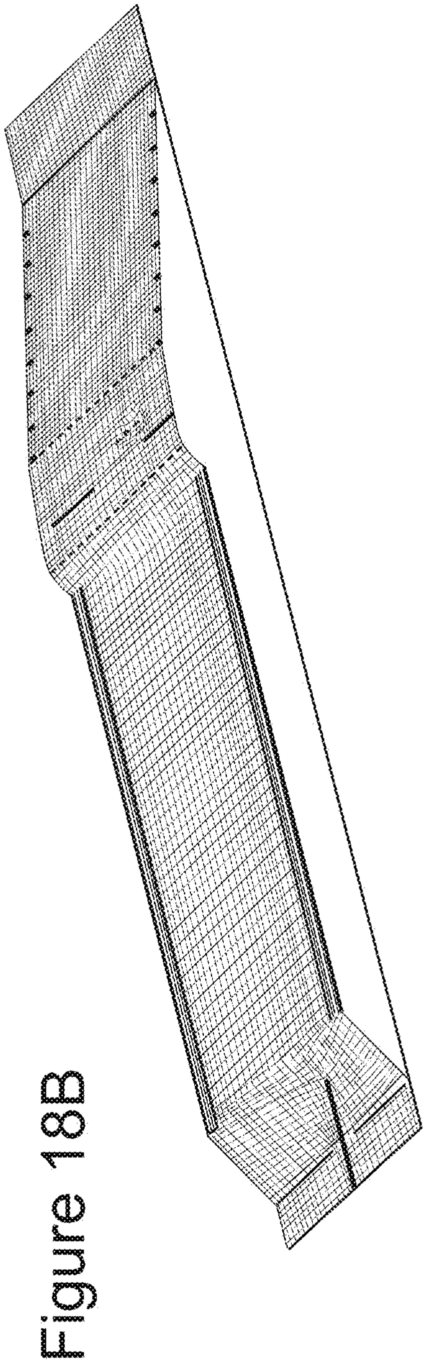

In FIG. 18A a gradual up slope electric field does not block charged particles as efficiently as in other embodiments. FIG. 18B illustrates the resulting slowly rising potential energy surface generated by the embodiment illustrated in FIG. 18A which does not include a grid attached to the exit end of the first chamber or at the end of the jet relaxation region, as previously explained.

Once an optimal drift tube configuration is designed, it remains possible to improve resolution by incorporating knowledge of the physical mechanisms that degrade performance, such as multiple charging, diffusion and gate spread, and flow velocity variations. If the spread mechanisms are approximately constant and known, deconvolution methods can be used to correct for non-ideal effects. For example, if by measurement calibration or calculation the shape of the actual arrival time distribution for a discrete particle size is determined, it will be possible to post-process full length TOF spectra and correct for the arrival time spread, as explained next.

The ideal current at a given time is specified by the number of particles of size and charge related to the TOF. However, because of the resolution factors described above, there is a spread in arrival times due to diffusion and non-ideal background flow velocity variations. However, once a flow geometry has been defined, the resulting TOF spread function for each size can be measured and/or modeled. Thus the current measured at each time is a convolution of different particle sizes and charge levels.

For specified instrument operating conditions, the relationship between particle drift velocity, $V_d$ and particle size, $d_p$ is given by:

$$V_d = C \times \frac{1}{d_p^2} = \frac{l}{t_d}, \tag{1}$$

where / is the drift tube length, and $t_d$ is the drift time. The drift time in turn is related to the measured particle velocity $V_p$ by $V_d = V_p - V_g$, where $V_g(r,x)$ is the gas velocity experienced by each particle size. For matrix deconvolution, the canonical form of Eq. (1) is used to characterize the correct form of size binning so that $$\frac{\Delta V_d}{V_d} = -\frac{\Delta t_d}{t_d} = \frac{\Delta\left(\frac{1}{d_p^2}\right)}{\left(\frac{1}{d_p^2}\right)} = -\frac{2\Delta d_p}{d_p}. \tag{2}$$

To give a size resolution of 100 or greater, the time bins should be scaled to give $\Delta t_d/t_d < 0.02$. This measurement accuracy can readily be achieved.

Using the above time and size scaling conditions, one can then write a recursive set of equations that relates the charged particle number count per unit time, $C_n$ (or measured charged particle current) at a measured time interval following charged particle release from the electrode gate to the flow of various charged particle sizes in the drift tube. The charged particle flow $C_n$ is given by the convolution of charged particles of different sizes traversing different trajectories at varying gas velocities, yet arriving in the same time bin, $C_n(1/t_n)$ with time width defined in Eq. (2). In the following, the number concentration density, $N_n(1/d_n^2)$, also has a bin width defined by Eq. (2). In the following, the charged particle concentration $N_n$ for all sizes is assumed to be uniform. If the charged particle are not uniformly distributed in the grid trap prior to release, the following equations can readily be modified by a weighting function (of radius) that accounts for the radial distribution of charged particles and trajectories.

The primary equation for arbitrary $C_n$ is written algebraically, following the general method described by Holve and Self (Holve, D., and Self, S. "Optical particle sizing for in situ measurements: Parts 1 and 2, Applied Optics, 18(10), 1632-1652, 1979, the contents of which are incorporated herein in their entirety by reference):

$$C_n(1/t_n) = Q_{n,n}N_n + Q_{n,n+1}N_{n+1} + \ldots + Q_{n,n+j}N_{n+j} \tag{3}$$

Here, the volumetric flow of charged particles follows a specific trajectory of specified gas and drift velocity in a symmetric area annulus around the axis of the drift tube, i.e., $$Q_{n,k}\left[\frac{\text{cm}^3}{s}\right] = V_{nk}\Delta S_n, \tag{4}$$

where $V_{nk}$ (cm/s) is the particle velocity corresponding to the sum of the average gas velocity, $V_{gi}$(rn) (integrated over the drift tube length) at a defined radius, plus the charged particle drift velocity $V_d$(dk). The cross-section, $\Delta S_k$ [$cm^2$] is dependent only on the radius, and not on the charged particle size (=2πrn Δrn).

Thus smaller charged particles (with faster drift velocities) traveling on slower gas velocity trajectories at larger radius can have the same total particle velocity and arrive at time interval $t_n$. The number of terms, j, in the sum depends on the overall range of possible gas velocity trajectories that hit the detector ranging from r=0 to $r_d$. This also determines the size range of faster charged particles that can arrive at the time interval $t_n$.

For a specified set of drift tube instrument parameters (pressure, voltage, and geometry), the values of $Q_{n,k}$ can be determined through CFD calculations for each particle size. Once these values are specified, the system of equations represented in Eq. (3) can be readily solved by back substitution. These equations range from $C_1$ and $d_1$, which is the slowest and largest particle of interest (longest transit time), to the fastest charged particles of interest, $C_m$ and dm. Back substitution begins with the fastest charged particles that have little or no overlap in transit time with other charged particles so that the initial conditions for starting the solution is just 1 term, i.e.:

$$C_n(1/t_m)=Q_{m,m}N_m. \qquad (5)$$

As mentioned above, if the charged particles are not uniformly distributed in the trap, which is likely to be the case for a particular embodiment, a weighting function $w_n$(rn) can be incorporated to multiply each $Q_{n,k}$ by $w_n$ ($\Sigma w_n \leq 1$) so as to account for the non-uniform distribution of charged particles with radius. This weighting function can be determined by using the results of CFD calculations that determine the radial gas velocities, coupled with a charged particle flow simulation program (e.g., Simion) that calculates the radial distribution of charged particle sizes at the electrode gate prior to release into the drift tube. Thus if the population of particles is confined to a smaller radial annulus, the variation of gas velocity and charged particle sizes that can contribute to a measured $C_n$ is reduced, thereby increasing the initial size resolution prior to deconvolution. Note that the charged particle distribution sum is less than or equal to 1, accounting for possible radial loss of charged particles.

Furthermore, the above-summarized equations can also be modified to include multiple charging effects if they are significant. The drift velocities are proportional to the square root of the charge, which in the above analysis is assumed to be 1. However, if there are multiple charged particles that potentially overlap slower drift particles, these terms can be added to the set of equation represented by Eq. (3), correcting the final result for faster particle overlap on larger particle sizes. The probabilities of multiple charging have been calculated by Fuchs (see, for example, Fuchs, N. A. (1963), On the Stationary Charge Distribution on Aerosol Particles in a Bipolar Ionic Atmosphere, Geofisica Pura e Applicata, 56, 185, the contents of which are incorporated herein by reference in their entirety). The number concentrations in each size bin ($N_i$) may be readily converted to standard number concentration frequencies, dN/dlogd.

Eq. (3) can be simplified to varying degrees, the simplest being the assumption that $C_n$ is related to one average particle size traversing the drift tube at one average drift and gas velocity. This effectively corresponds to a rolling average solution of all the terms up to index j, with one overall term in each row equation. This is the method currently used to show the results given by current experimental measurements further described below, but those of ordinary skill in the art will understand that this assumption is not intended to limit the scope of the subject matter disclosed herein in any way. As will be explained further below, the effects of particle overlap increase with increasing size, thereby reducing resolution. However, once the instrument geometry is defined and optimal configuration determined, it is straightforward to incorporate all the known parameters, and to solve the set of equations represented by Eq. (3) iteratively and rapidly in real time to obtain significantly improved high resolution results for all particle sizes of interest.

Figure 13:
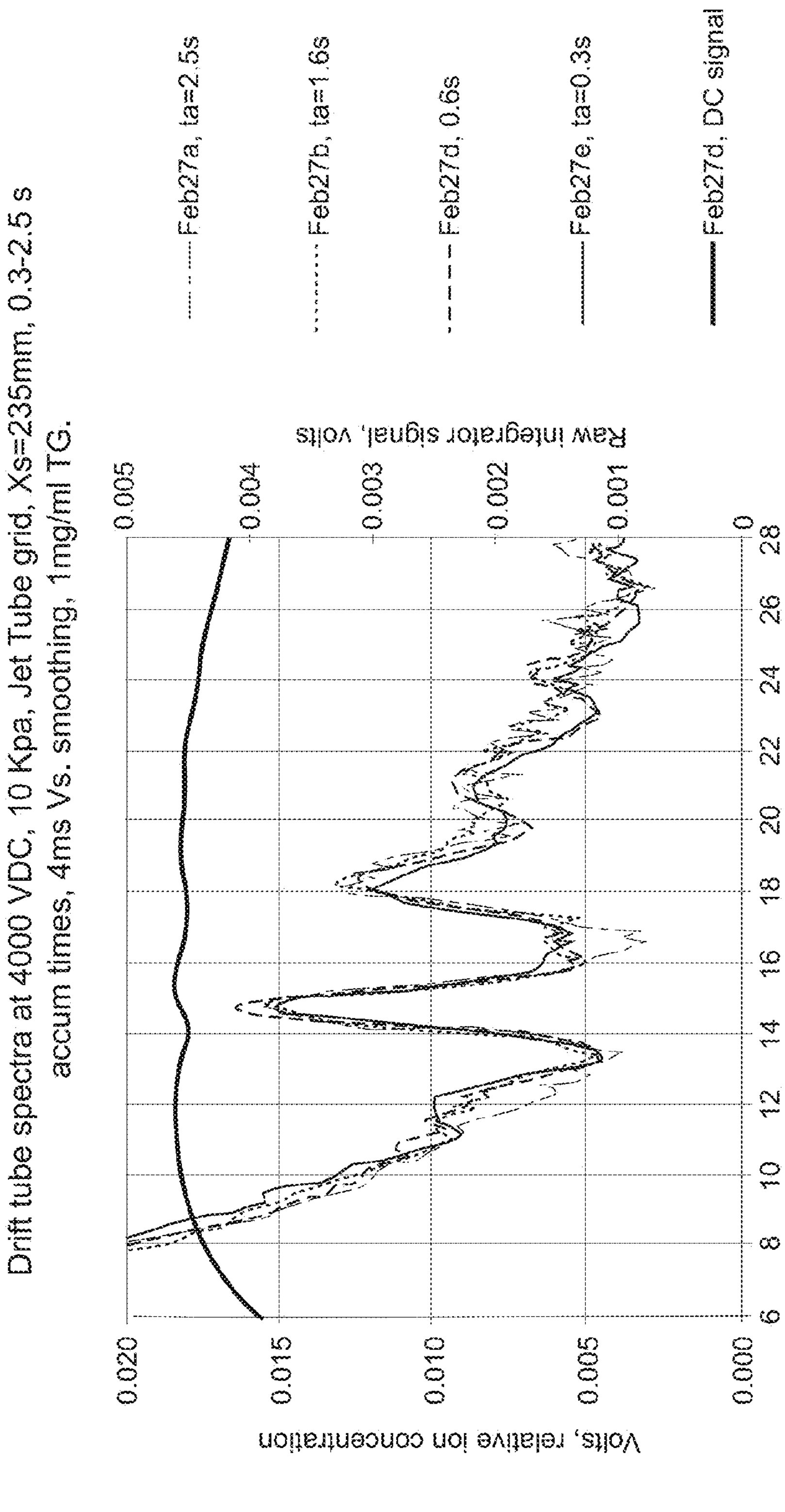
FIG. 13 illustrates a variation of various voltage signals as a function of time for experimental results of size measurements using a drift tube according to an exemplary embodiment of the subject matter disclosed.

In order to illustrate the effect of the above-summarized advantageous deconvolution, experiments were performed using particles of a known size. It should be understood that these results are not presented here to limit the subject matter disclosed, but simply to illustrate the contents of this disclosure. FIG. 13 illustrates repeated measurements of an electrosprayed solution of Thyroglobulin (TG) monomer at P=10 kPa and specified Drift Tube parameters. This figure shows the relative population of charged particles (represented by measured voltage signal) at various charged particle arrival times at the detector. Using Eqs. (1) and (6), along with CFD values of the average background gas velocity, the arrival times can be converted to equivalent particle sizes as shown on the X axis. The measured DC signal is the output of the detector integrating amplifier, which is converted to an equivalent input charged particle voltage as a function of time. The primary monomer peak occurs at 14.8 nm and independent measurements by differential mobility (DMA and CNC) methods give a value of 14.9 nm. Subsequent population peaks occur within 2% of the theoretical volume average diameter. These larger size populations occur in some (but not all) measurements because the concentration of TG may not be sufficiently dilute to capture one monomer per electrosprayed droplet, or the electrospray may generate a different distribution of solvent droplets. Resolution of two adjacent size populations is equally desired as measurement of absolute size, and the results clearly show this capability with R=40 for the monomer.

Given the variation in electrospray conditions, some variation in results is expected. Repeat measurements for fixed instrument parameters are very precise, within 1% or so of the indicated size. Peak Raw signal levels for the experimental measurement results shown in FIG. 13 are on the order of 5 mv, with a noise level of ±1 my for a single scan. Pump noise at 60 Hz can be eliminated by proper vibration isolation.

The results above are based on 512 repeat scans, each of which is 0.6 seconds long, or a total of 5 minutes. The electrode gate accumulates and stops particle flow for 0.6 seconds (a variable) and then releases the particles into a stable electric and background gas flow field that transports the small particles faster than the large ones, giving a signal (proportional to the number of charged particles at each size) that is a function of time. This repeat scan process improves the S/N by sqrt(512), or by a factor of 22 over a single 0.6 second scan. With an optimized A/D design and processing, the computational overhead will be negligible, and spectra will display in real time. The fact that the signal/noise keeps improving with increased number of scans shows how stable the supersonic jet and gas flow is in the system, along with the switching high voltage system of the electrode gate. For these exemplary measurements, the output of the detector integrating amplifier signal is cabled to an oscilloscope, where the end result is downloaded into an Excel file.

For the exemplary measurements just shown, the computation comprises the following steps. First, rolling average smoothing of integrator output data following a numerical differentiation of the smoothed data. Secondly, summing the integrator output and the differentiated signal (times feedback constant=0.5 sec), leading to the input charged particle voltage as a function of time (10,000 data points from the particular data acquisition system used in these exemplary measurements). Subsequently, converting the time scale to size, $d_p$=C* Sqrt ($E/PV_d$), where C is a constant (including viscosity), E is electric field (volts/cm), P is the DT pressure, and $V_d$ is the drift given the difference in particle and gas velocities, i.e., $V_p-V_{gavg}$. $V_p$, is given by $l/t_m$, is the measured particle velocity detected as time in the data acquisition system, $t_m$, and l is the drift tube length. $V_{gavg}$(r) is the average gas velocity at each radial trajectory from the electrode gate to the detector (9 cm in this embodiment), and varies with axial position, x, and radius r. If $V_d$>>$V_{gavg}$, then using a constant value is a good approximation. Currently, all the calculations use a constant value, so the size is not as accurate for larger particles above 20-30 nm, but those of ordinary skill will know readily how to relax this assumption based on the subject matter disclosed.

In assessing accuracy and error analysis for the exemplary experimental results just described, the general formula above can be re-arranged to give explicit results in terms of time, i.e.:

$$d_p = C\sqrt{\frac{Et_m}{Pl} \times \frac{t_g}{t_g - t_m}}. \quad (6)$$

In Eq. (6), if the drift velocity is fast relative to the background gas velocity, (i.e., $t_g$>>$t_m$ or tg/(tg−tm)≈1), sizing accuracy is just dependent on accuracy of time measurements, $t_m$, E, P, and l. These values can be specified to better than 2%. For large particles the greatest uncertainty is the variation in $t_g$, giving an absolute uncertainty around 8% for 50 nm particles.

Figure 14:
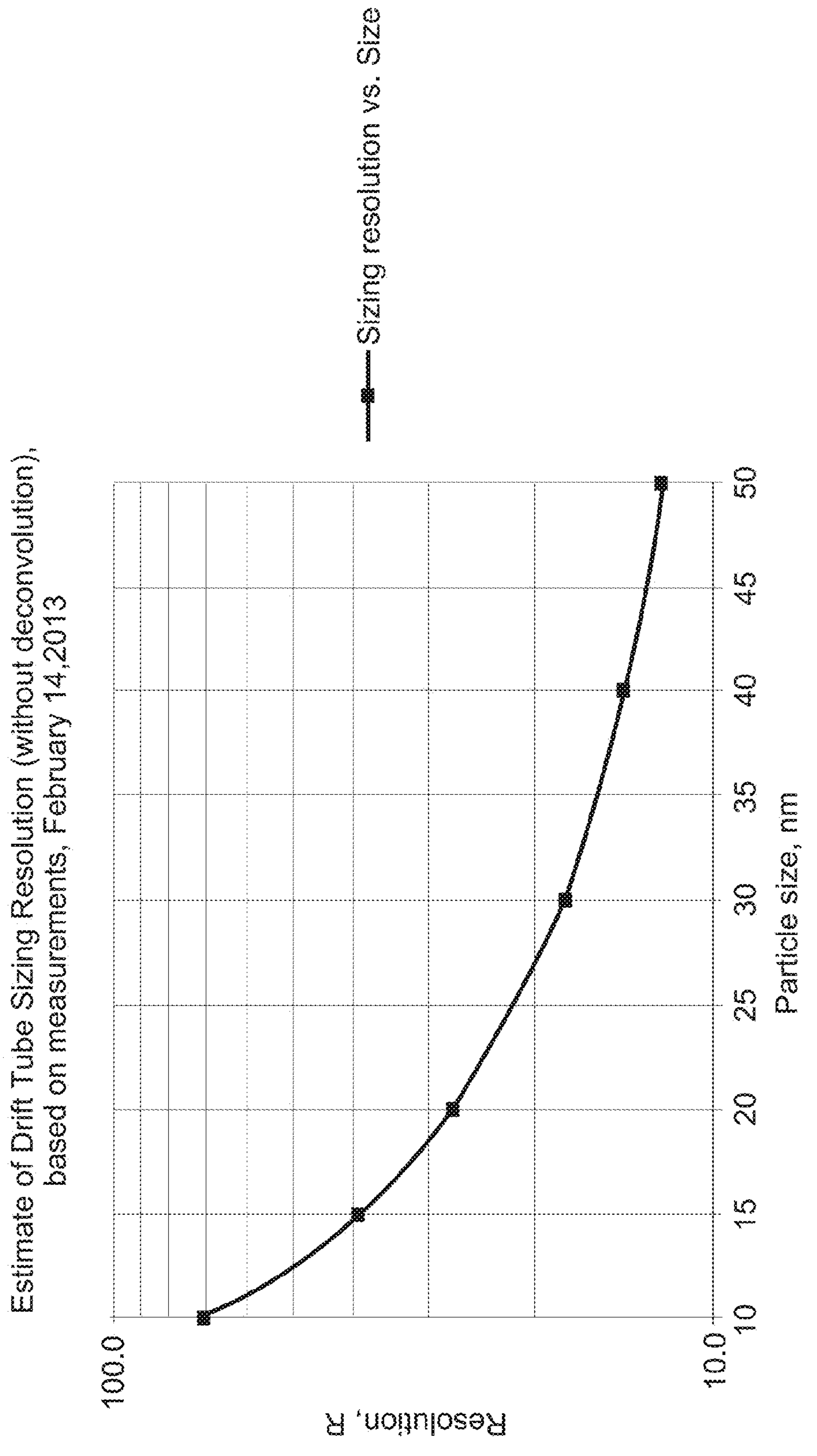
FIG. 14 illustrates a variation of resolution as a function of particle size based on experimental measurements using a drift tube according to an exemplary embodiment of the subject matter disclosed.

FIG. 14 illustrates an estimate of measurement resolution as a function of size for the exemplary measurements just described. As already explained, a mathematical deconvolution method can be used to further improve the accuracy and resolution for all sizes, and is discussed further below. It is important to note that these calculations are all "first principles" calculations, with no calibration constants.

In order to obtain maximum resolution a more detailed evaluation of the variation in $V_g$(x,r) is desired, which is given by the CFD calculations already explained. The radial velocity values in the jet expansion region explain why charged particles (and signal) are lost radially in a conventional electrode gating system. These radial velocities in the region of the electrode gate are on the order of 10 cm/s, and show that the maximum charged particle accumulation times are on the order of 50-100 ms. At longer times they flow to the wall outside the 1.5 cm detector radius, and are not measured. A modified focusing electrode and trapping grid has been designed (using Simion) to constrain all particles within a specified detector diameter, (currently 35 mm), eliminating or substantially reducing radial charged particle loss, and boost signal levels by an estimated factor of ten or more.

Figure 15:
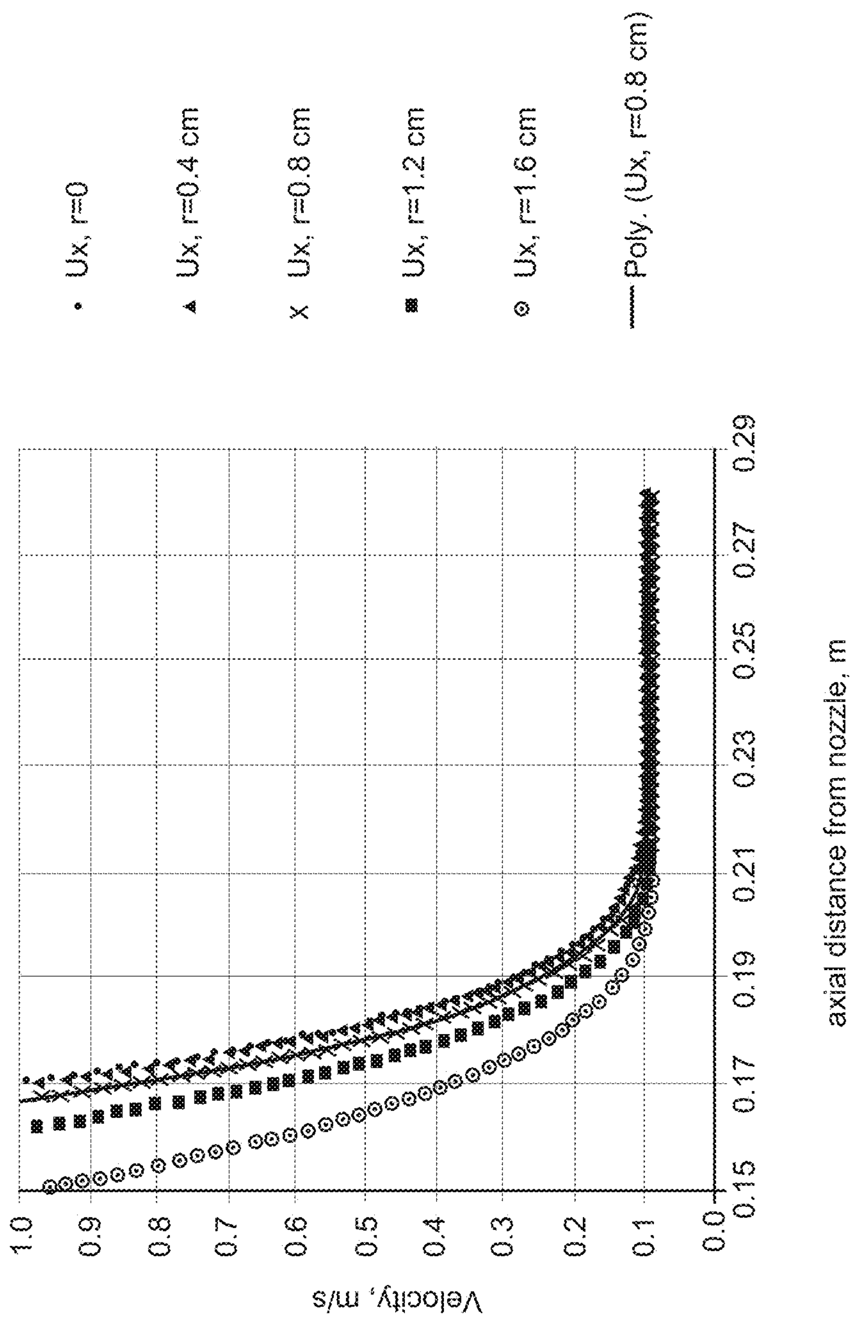
FIG. 15 illustrates various axial velocity profiles computed for a drift tube according to an exemplary embodiment of the subject matter disclosed.

FIG. 15 shows the axial velocity profiles in x, as a function of r. The nozzle is placed at a point where the velocity is less than 20 cm/s, approximately 200 mm from the nozzle exit. The initial gas velocity at the trapping grid can vary significantly, although the average velocity variation integrated over x is less than 10%. Nevertheless, this variation becomes more important for larger sizes, where $V_d$ is comparable to $V_{gavg}$, and as seen in the resolution chart, degrades resolution with increasing size. This is where the deconvolution method will provide an advantageous improvement in size measurement. Current measurements are taken at about 60% of original design voltages, and the size resolution improves roughly proportional to the Sqrt (voltage) because the drift velocity increases relative to the $V_{gavg}$. Optimum operating conditions consistent with Paschen limits on corona discharge (increasing with pressure) can be used in other embodiments.

Figure 22:
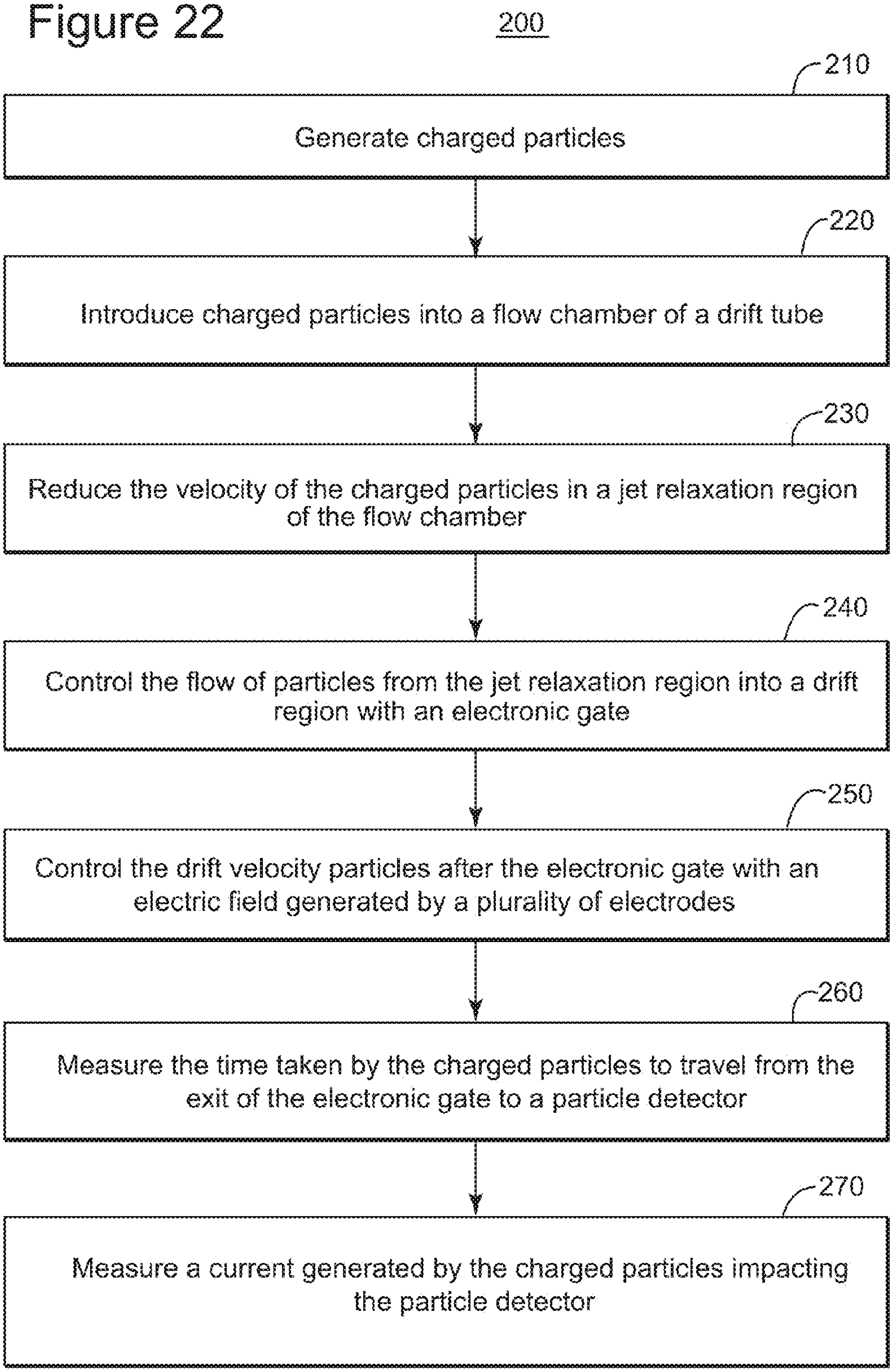
FIG. 22 illustrates the flow chart of an exemplary embodiment of a process or method for measuring particle size and concentration.

The subject matter disclosed herein also includes methods and processes to measure size and concentration of particles. FIG. 22 illustrates an embodiment of such a process in the flowchart of method 200. As illustrated, a first step of method 200 includes the step 210 of generating charged particles with a particle source. Such a source could be operated in atmospheric pressure or any other desired pressure. In step 220, the generated particles are introduced into a flow chamber of a drift tube operating at a pressure lower than atmospheric pressure. In step 230, the velocity of the charged particles is reduced in a jet relaxation region of the flow chamber while the particles are maintained along a centerline of the chamber. In step 240, the flow of particles from the jet relaxation region into a drift region of the chamber is controlled by use of an electronic gate. In step 250, the drift velocity of the particles allowed to pass through the electronic gate is controlled with an electric field generated inside the drift region by a plurality of electrodes. In step 260, measurement is made of the time taken by the charged particles to travel from the exit of the electronic gate to a particle detector disposed at a distal end portion of the chamber. Finally, in step 270, a current generated by the charged particles impacting the particle detector is measured, wherein a measurement of size and concentration of the charged particles is based on the current generated by the charged particles and the time taken the charged particles to travel from the electronic gate to the detector.

Based on the subject matter disclosed herein and the exemplary method disclosed in FIG. 22, those of ordinary skill will appreciate many variations of methods and processes that are within the scope of this disclosure. Some non-limiting examples of such methods are briefly summarized herein. For example, a method for predicting the time it takes particles to travel between an electronic gate and the exit of the second chamber, using computational fluid dynamics, to guide the deconvolution process already explained. Second, a method for improving the accuracy of measurements using the predictions of correct the data using the disclosed deconvolution approach. Another example includes a method for converting the time predictions into particle size distributions, as previously explained. Another exemplary method will include using the converted time predictions into particle size distribution to characterize particles isolated from human or animal serum. Another method includes the use of such characterizations to assess human or animal health, to characterize particles released from combustion sources, to determine the molecular cross-section of molecules from TOF calculations, including determination of molecular conformation for the purpose of assessing protein function, and a method for rapidly analyzing protein mixtures without the need for calibration substances.

Figure 21:
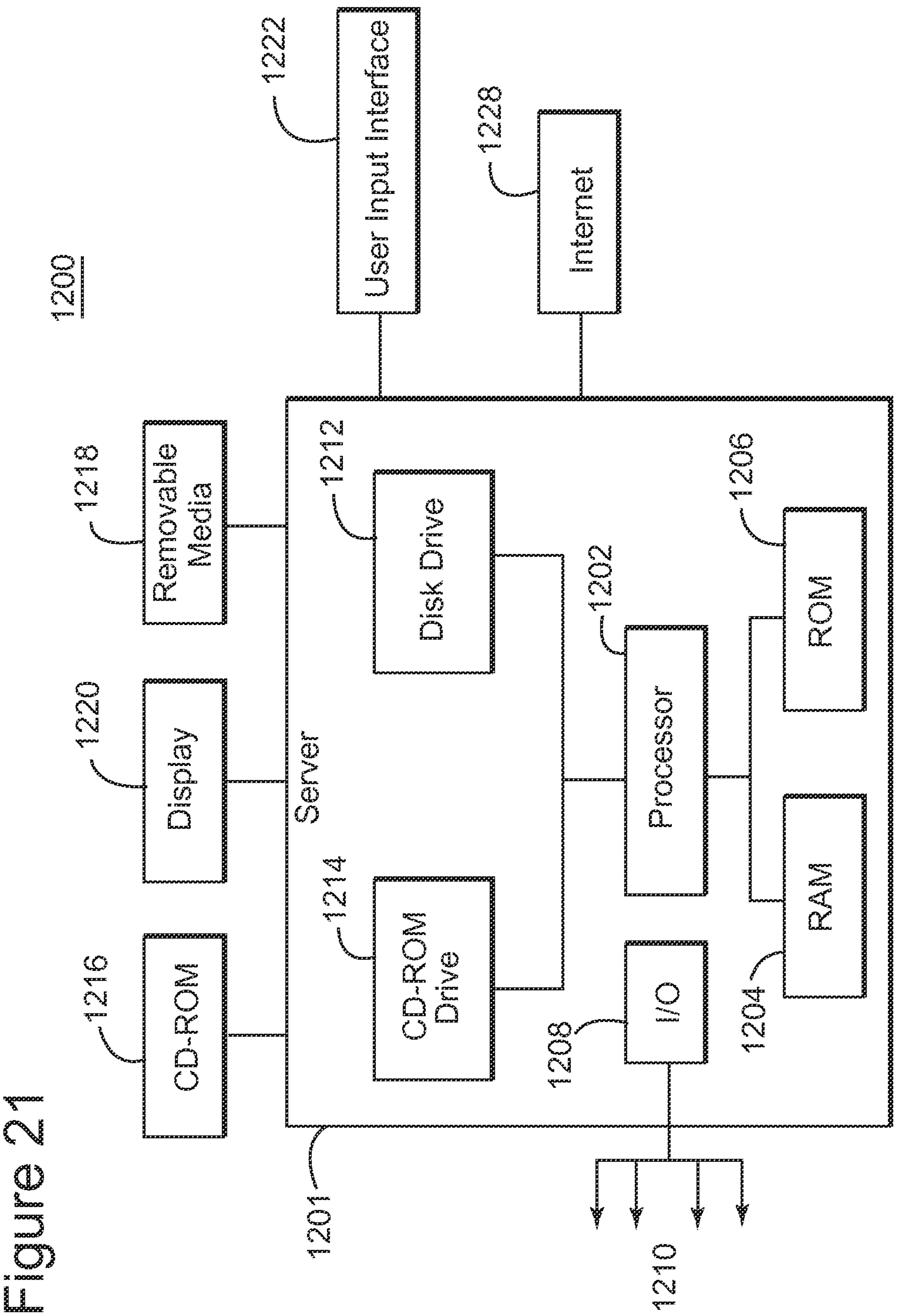
FIG. 21 illustrates a schematic diagram of a computing device configured to run methods according to the various embodiments of the subject matter disclosed.

One or more of the steps of the methods comprising the subject matter disclosed may be implemented in a computing system specifically configured to calculate the size and concentration of charged particles as explained hereinabove. An example of a representative computing system capable of carrying out operations in accordance with the exemplary embodiments is illustrated in FIG. 21. Hardware, firmware, software or a combination thereof may be used to perform the various steps and operations described herein. The computing system may be one of elements 126, 128 and 129 or may be implemented in one or more of these elements.

The exemplary computing system 1200 suitable for performing the activities described in the exemplary embodiments may include server 1201. Such a server 1201 may include a central processor (CPU) 1202 coupled to a random access memory (RAM) 1204 and to a read-only memory (ROM) 1206. The ROM 1206 may also be other types of storage media to store programs, such as programmable ROM (PROM), erasable PROM (EPROM), etc. The processor 1202 may communicate with other internal and external components through input/output (I/O) circuitry 1208 and bussing 1210, to provide control signals and the like. The processor 1202 carries out a variety of functions as is known in the art, as dictated by software and/or firmware instructions.

The server 1201 may also include one or more data storage devices, including a hard drive 1212, CD-ROM drives 1214, and other hardware capable of reading and/or storing information such as DVD, etc. In one embodiment, software for carrying out the above discussed steps may be stored and distributed on a CD-ROM 1216, removable memory device 1218 or other form of media capable of portably storing information. These storage media may be inserted into, and read by, devices such as the CD-ROM drive 1214, the disk drive 1212, etc. The server 1201 may be coupled to a display 1220, which may be any type of known display or presentation screen, such as LCD displays, LED displays, plasma display, cathode ray tubes (CRT), etc. A user input interface 1222 is provided, including one or more user interface mechanisms such as a mouse, keyboard, microphone, touch pad, touch screen, voice-recognition system, etc.

The server 1201 may be coupled to other computing devices, such as the landline and/or wireless terminals via a network. The server may be part of a larger network configuration as in a global area network (GAN) such as the Internet 1228, which allows ultimate connection to the various landline and/or mobile client devices. The computing device may be implemented on a vehicle that performs a land seismic survey.

Exemplary embodiments of software comprising the subject matter disclosed include those to analyze charged particle samples automatically. The software may be configured control a pipetting robot to dispense samples into 96 well plates, from which aliquots are removed and treated with standard chemical methodologies to isolate lipoproteins from serum, or whatever might be analyzed by this method. Further automated pipetting steps, controlled by software, may deliver purified lipoproteins to a fresh 96 well plate that will be stored for later analysis by drift tube mobility spectrometry. The stored samples may be further processed to deliver them to an electrospray source that pumps the lipoprotein sample at a controlled flow rate for the purpose of generating gas-borne lipoproteins that are drawn into the drift tube.

Furthermore, these software products may record the output of the drift tube detector, apply various algorithms to clean the data, such as smoothing, and may then mathematically process the output signal to generate a secondary signal that can be further processed mathematically to produce charged particle mobility spectra. The spectra may be treated with deconvolution algorithms to generate information useful to classify lipoproteins according to the way cardiologists use particle size analysis to diagnose coronary heart disease and establish medical treatment regimens for these or other applicable health conditions.

Software products are also within the scope of the subject matter disclosed that will generate a plurality of reportable summaries. A first example is a software to interface into the laboratory information management system of analytical labs. A second example is a software appropriate for communicating test results to the prescribing physician and to the patient.

The disclosed exemplary embodiments provide apparatuses, methods, and systems for measuring size and concentration of charged particles as well the other uses herein-above summarized. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

While the disclosed embodiments of the subject matter described herein have been shown in the drawings and fully described above with particularity and detail in connection with several exemplary embodiments, it will be apparent to those of ordinary skill in the art that many modifications, changes, and omissions are possible without materially departing from the novel teachings, the principles and concepts set forth herein, and advantages of the subject matter recited in the appended claims. Hence, the proper scope of the disclosed innovations should be determined only by the broadest interpretation of the appended claims so as to encompass all such modifications, changes, and omissions. In addition, the order or sequence of any process or method steps may be varied or re-sequenced according to alternative embodiments. Finally, in the claims, any means-plus-function clause is intended to cover the structures described herein as performing the recited function and not only structural equivalents, but also equivalent structures.

What is claimed is:

1. An apparatus for measuring size and concentration of particles, the apparatus, comprising:

a body having proximal and distal end portions, said body defining a chamber through which charged particles may flow, said body being configured to operate at a pressure below an atmospheric pressure;

an end cap disposed on the proximal end portion of the body, the end cap having an orifice;

an exhaust port disposed on the distal end portion of the body;

a particle detector disposed inside of the chamber adjacent to the exhaust port;

a particle source disposed outside of the chamber adjacent to the orifice, said particle source being configured to generate the charged particles at atmospheric pressure;

a focusing electrode disposed inside of the chamber, said focusing electrode being configured to minimize lateral dispersion of the charged particles inside of the chamber;

an electronic gate disposed downstream of the focusing electrode, said electronic gate being configured to trap and release the charged particles as they flow inside of the chamber, said focusing electrode and said electronic gate further dividing the chamber into a jet relaxation region between the end cap and the focusing electrode and a drift region between the electronic gate and the particle detector;

a plurality of electrodes disposed on the body in the drift region downstream of the electronic gate, said plurality of electrodes being configured to generate an electric field inside the chamber so as to control drift velocities of the charged particles released from the electronic gate towards the particle detector; and a timing device configured to measure a time taken by the charged particles to travel from the electronic gate to the particle detector, wherein a measurement of the size and concentration of the charged particles is based on an output signal from the particle detector and the time measured by the timing device.

2. The apparatus according to claim 1, wherein a diameter of the orifice ranges from about 10 to about 1000 μm, the charged particles being configured to enter the chamber through the orifice at chocked flow conditions.

3. The apparatus according to claim 1, wherein the electronic gate further comprises first, second, and third electrically conducting grids separated from one another by dielectric spacers.

4. The apparatus according to claim 3, wherein the electronic gate is configured to operate in a particle blocking mode, a particle trapping mode, or a particle injecting mode.

5. The apparatus according to claim 4, wherein the electronic gate further comprises a voltage source connected to the electrically conducting grids and the focusing electrode, the voltage source being configured to generate static or pulsed voltage signals to control an operating mode of the electronic gate.

6. The apparatus according to claim 5, further comprising:

A second focusing electrode disposed between the first and second electrically conducting grids, the second focusing electrode being configured to minimize lateral dispersion of the charged particles.

7. The apparatus according to claim 1, further comprising:

a grid disposed upstream of the particle detector, said grid being configured to minimize a registering of a current signal at the particle detector before the charged particles impact the particle detector.

8. The apparatus according to claim 1, wherein the plurality of electrodes in the drift region further comprises a plurality of electrically conducting axially aligned disks having centered holes connected in an arrangement where the disks are separated from each other by axially aligned dielectric disks with centered holes, wherein the plurality of electrically conducting axially aligned disks is sealed together in an arrangement forming the body in the shape of a tube configured to pass a flow of gas towards the particle detector, wherein an entrance to the tube is connected to the electronic gate by a dielectric spacer.

9. The apparatus according to claim 1, wherein the exhaust port is connected to a vacuum pump through a porous metal wall, said vacuum pump being configured to lower the pressure inside the chamber.

10. The apparatus according to claim 1, wherein the particle detector further comprises a porous metal plate connected to an ammeter, the porous metal plate being further connected to an end portion of the chamber in the drift region by a dielectric spacer ring.

11. The apparatus according to claim 10, wherein a measurement of a current detected by the ammeter generated by charged particles striking the porous metal plate starts when a pulsed voltage is applied to the electrode gate and continues until a majority of the charged particles gated into the drift region strike the porous metal plate.

12. The apparatus according to claim 1, wherein the body further comprises an electrode tube disposed in the jet relaxation region, said electrode tube being configured to generate an electric field inside the chamber so as to prevent small particles from flowing into the drift region of the chamber to the particle detector.

13. The apparatus according to claim 1, further comprising:

a detector grid disposed upstream of the particle detector, the detector grid being configured to minimize or eliminate a registering of a current signal at the particle detector before the charged particles impact the particle detector.

14. The apparatus according to claim 1, further comprising:

a first valve connected to the exhaust port of the body, the first valve being configured to be closed so as to allow particle size measurements to be made in a substantially stagnant environment inside the apparatus.

15. The apparatus according to claim 1, further comprising:

a first valve connected to the exhaust port of the body and a second valve connected to the end cap of the body, wherein, before the charged particles accumulated in the electronic gate are released toward the drift region, both the first and second valves are open and a countercurrent flow of a clean gas is introduced from the first valve toward the second valve so as to flush out solvent vapors from the apparatus, and, wherein, the first and second valves are subsequently closed so as to allow measurements to be made in a substantially stagnant environment inside the apparatus.

16. The apparatus according to claim 1, further comprising:

a processor configured to deconvolve a spread in arrival times generated by charged particles of different sizes and charge levels and variations of a flow velocity of a background gas to arrive at the measurement of a size and concentration of the charged particles.

17. The apparatus according to claim 16, wherein a deconvolution carried out by the processor takes into account a flow geometry of the apparatus.

18. The apparatus according to claim 1, wherein the charged particles are selected from the group comprising smoke particles, dust particles, nanoparticles, assemblies of molecules, clusters of protein and/or lipid molecules, atmospheric aerosols, nanolipid particles, nanolipid disks, and clumps of such particles.

19. The apparatus according the claim 1, wherein the focusing electrode is positioned inside of the chamber in a location where axial velocities of the charged particles are low so as to allow the electronic gate to stop them from flowing toward the particle detector when the electronic gate is actuated.

20. A method for measuring size and concentration of particles, the method comprising:

generating charged particles with a particle source operating at an atmospheric pressure;

introducing the generated charged particles into a flow chamber formed by a body of a drift tube operating at a pressure lower than atmospheric pressure, the body having an end cap disposed on a proximal end portion of the body and an exhaust port disposed on a distal end portion of the body, the end cap having an orifice through which the charged particles are introduced into the flow chamber;

reducing a velocity of the charged particles in a first portion of the flow chamber while maintaining the charged particles flowing along a centerline of the body;

controlling a flow of the charged particles from the first portion of the flow chamber to a second portion of the flow chamber by an electronic gate;

controlling the velocity of the charged particles through the second portion of the flow chamber with an electric field generated inside the second portion of the flow chamber by a plurality of electrodes;

measuring a time taken by the charged particles to travel from the exit of the electronic gate to a particle detector disposed adjacent to exhaust port; and measuring a current generated by the charged particles impacting the particle detector, wherein a measurement of size and concentration of the charged particles is based on the current generated by the charged particles and the time taken the charged particles to travel from the electronic gate to the particle detector.

* * * * *